(12) United States Patent
Fox

(10) Patent No.: US 9,451,957 B2
(45) Date of Patent: Sep. 27, 2016

(54) BONE STAPLE EXTRUSION INSTRUMENT AND METHOD OF USE AND MANUFACTURING

(71) Applicant: William Casey Fox, Pipe Creek, TX (US)

(72) Inventor: William Casey Fox, Pipe Creek, TX (US)

( * ) Notice: Subject to any disclaimer, the term of this patent is extended or adjusted under 35 U.S.C. 154(b) by 635 days.

(21) Appl. No.: 13/835,277

(22) Filed: Mar. 15, 2013

(65) Prior Publication Data

US 2013/0206815 A1    Aug. 15, 2013

Related U.S. Application Data

(63) Continuation-in-part of application No. 13/192,162, filed on Jul. 27, 2011, and a continuation-in-part of application No. 13/192,177, filed on Jul. 27, 2011, now abandoned, and a continuation-in-part of application No. 13/192,186, filed on Jul. 27, 2011, now Pat. No. 9,017,331, and a continuation-in-part of application No. 13/192,198, filed on Jul. 27, 2011, now Pat. No. 9,339,268.

(60) Provisional application No. 61/759,327, filed on Jan. 31, 2013.

(51) Int. Cl.
*A61B 17/068* (2006.01)
*A61B 17/064* (2006.01)
*A61B 17/00* (2006.01)

(52) U.S. Cl.
CPC ....... *A61B 17/0682* (2013.01); *A61B 17/0642* (2013.01); *A61B 2017/00867* (2013.01)

(58) Field of Classification Search
CPC ..... A61B 17/068; A61B 17/56; A61B 17/58
USPC ........................ 227/19, 175.1, 176.1; 606/75
See application file for complete search history.

(56) References Cited

U.S. PATENT DOCUMENTS 2,931,038 A    4/1960    Wandel
3,225,996 A    12/1965   Mallina
(Continued)

FOREIGN PATENT DOCUMENTS

WO    2013016633 A1    1/2013

OTHER PUBLICATIONS

Authorized Officer Lingfei Bai; Notification Concerning Transmittal of International Preliminary Report on Patentability with International Preliminary Report on Patentability and Written Opinion of the International Searching Authority, date of mailing Aug. 13, 2015; 12 pages.

(Continued)

*Primary Examiner* — Nathaniel Chukwurah
(74) *Attorney, Agent, or Firm* — Dickinson Wright PLLC; Ross Spencer Garsson

(57) ABSTRACT

A bone staple extrusion instruments used for fixation of bone and soft tissue of the musculoskeletal system and the methods for their use and manufacture. The bone staple extrusion instruments are used for insertion of staples into bones, which staples change shape through their metallurgic properties and the release from the bone staple extrusion instruments. In some embodiments, the bone staples pull together and compress bone once released from the bone staple extrusion instruments. In other embodiments, the staples push outward to place the bones in tension once released from the bone staple extrusion instrument.

24 Claims, 18 Drawing Sheets

(56) References Cited

U.S. PATENT DOCUMENTS

| | | | |
|---|---|---|---|
| 3,939,828 A | | 2/1976 | Mohr et al. |
| 3,960,147 A | | 6/1976 | Murray |
| 4,263,903 A | * | 4/1981 | Griggs ............... A61B 17/0642 227/147 |
| 4,414,967 A | | 11/1983 | Shapiro |
| 4,415,111 A | * | 11/1983 | McHarrie ............... A61B 17/92 227/147 |
| 4,438,769 A | | 3/1984 | Pratt et al. |
| 4,444,181 A | | 4/1984 | Wevers et al. |
| 4,485,816 A | * | 12/1984 | Krumme ............ A61B 17/0644 219/201 |
| 4,527,726 A | | 7/1985 | Assell et al. |
| 4,540,110 A | | 9/1985 | Bent et al. |
| 4,665,906 A | | 5/1987 | Jervis |
| 4,841,960 A | | 6/1989 | Gamer |
| 5,067,957 A | | 11/1991 | Jervis |
| 5,246,443 A | * | 9/1993 | Mai ................... A61B 17/0642 606/219 |
| 5,449,359 A | | 9/1995 | Groiso |
| 5,474,557 A | | 12/1995 | Mai |
| 5,779,707 A | | 7/1998 | Bertholet et al. |
| 5,853,414 A | | 12/1998 | Groiso |
| 6,059,787 A | | 5/2000 | Allen |
| 6,193,733 B1 | | 2/2001 | Adams |
| 6,268,589 B1 | | 7/2001 | Flot |
| 6,323,461 B2 | | 11/2001 | Flot |
| 6,325,805 B1 | | 12/2001 | Ogilvie et al. |
| 6,348,054 B1 | | 2/2002 | Allen |
| 6,685,708 B2 | | 2/2004 | Monassevitch et al. |
| 6,783,531 B2 | | 8/2004 | Allen |
| 7,240,677 B2 | | 7/2007 | Fox |
| 7,618,441 B2 | | 11/2009 | Groiso |
| 7,635,367 B2 | | 12/2009 | Groiso |
| 7,828,189 B2 | | 11/2010 | Holsten et al. |
| 8,596,514 B2 | | 12/2013 | Miller et al. |
| 2005/0043757 A1 | * | 2/2005 | Arad ................... A61B 17/0401 606/200 |
| 2005/0273108 A1 | | 12/2005 | Groiso |
| 2006/0058796 A1 | | 3/2006 | Hartdegen et al. |
| 2010/0023062 A1 | | 1/2010 | Faillace et al. |
| 2010/0036430 A1 | | 2/2010 | Hartdegen et al. |
| 2010/0125275 A1 | | 5/2010 | Kinmon et al. |
| 2010/0193569 A1 | | 8/2010 | Yates et al. |

OTHER PUBLICATIONS

Wright Medical; Charlotte Foot and Ankle Fixation System Brochure, SO 040-105 Rev. 04.06 (no month, 2005); Wright Medical Technology, Inc.; US.

BioPro, Inc.; The BioPro Memory Staple Brochure, Brochure No. 17704, rev. 2, (May 2010); BioPro; US.

DePuy Orthopaedics, Inc.; Memory Staple Brochure, Brochure 0612-00-584 (Rev. 1) (no month, 2006); DePuy Orthopaedics, Inc.; US.

MMI-USA, Easy Clip SI SuperElastic Fixation System Brochure, ECLP1000-rev D (Aug. 12, 2009), Memometal Inc., a Memometal Technologies, Inc.; US.

Biomedical Enterprises, Inc.; OSStaple Brochure, Brochure No. A108-076 (Rev B); (No Month 2010); BioMedical Enterprises, Inc.; US.

Patent Cooperation Treaty; PCT International Search Report, Issued in connection with PCT/US2012/048539; Oct. 18, 2012; 4 pages; US.

Patent Cooperation Treaty; PCT Written Opinion of the International Searching Authority, Issued in connection with PCT/US2012/048539; Oct. 18, 2012; 19 pages; US.

S.J. Warden et al.; Mechanotransduction in cortical bone is most efficient at loading frequencies of 5-10 Hz; Nov. 7, 2003; pp. 261-270; Elsevier Inc.; US.

C.H. Turner et al.; Basic Biomechanical Measurements of Bone: A Tutorial; (no month, 1993); pp. 595-608; Pergamon Press Ltd.; US.

Clinton T. Rubin et al.; Regulation of Bone Mass by Mechanical Strain Magnitude; (no month, 1985); pp. 411-417; Calcified Tissue International; US.

Alexander G. Robling et al.; Biomechanical and Molecular Regulation of Bone Remodeling; Apr. 3, 2006; pp. 455-498; The Annual Review of Biomedical Engineering; US.

Rich Lipschutz et al.; 510K Summary of Safety and Effectiveness, Fx Devices POGO Screw; Oct. 10, 2008; 5 pages; US.

Edmund Y.S. Chao et al.; Biophysical Stimulation of Bone Fracture Repair, Regeneration and Remodelling; (no month, 2003); pp. 72-85; vol. 6; European Cells and Materials; US.

A. Chamay et al.; Mechanical Influences in Bone Remodeling, Experimental Research on Wolff's Law; (no month, 1972); pp. 172-180; vol. 5; J. Biomechanics; Great Britain.

* cited by examiner

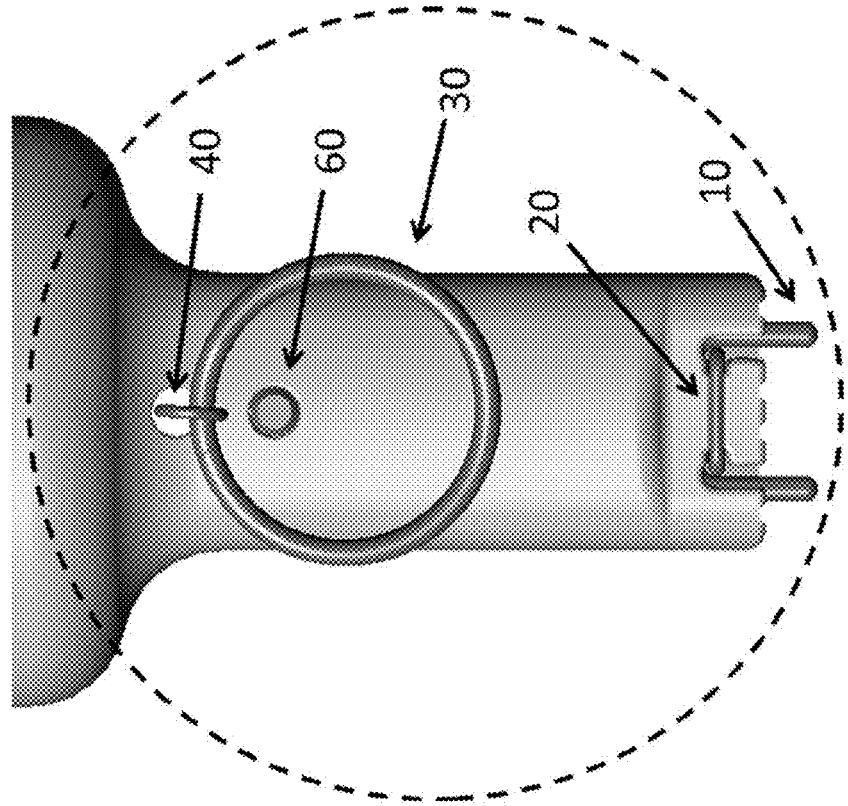
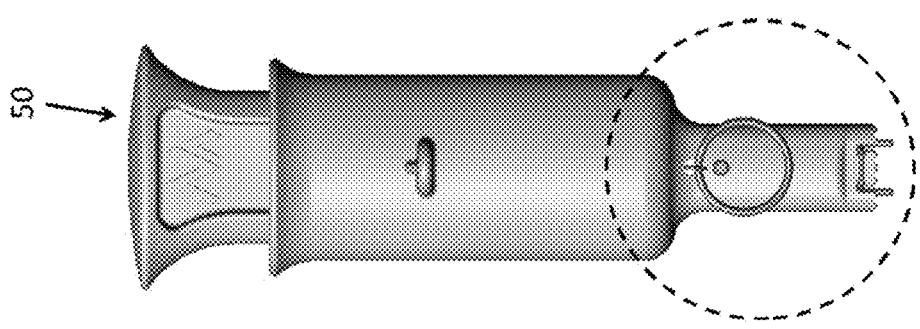
FIG. 3B
FIG. 3A

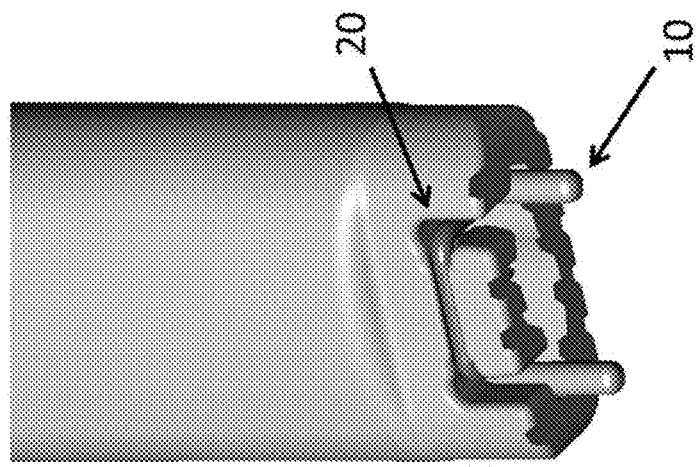
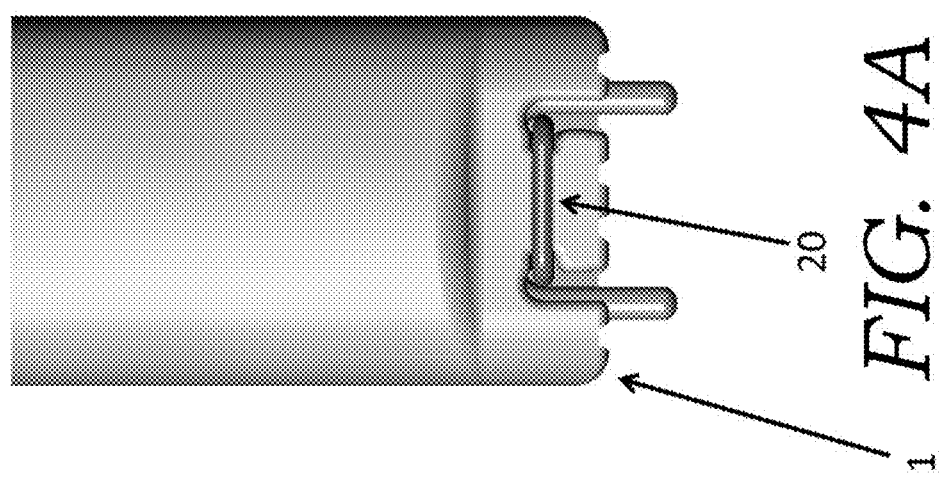
FIG. 4A
FIG. 4B

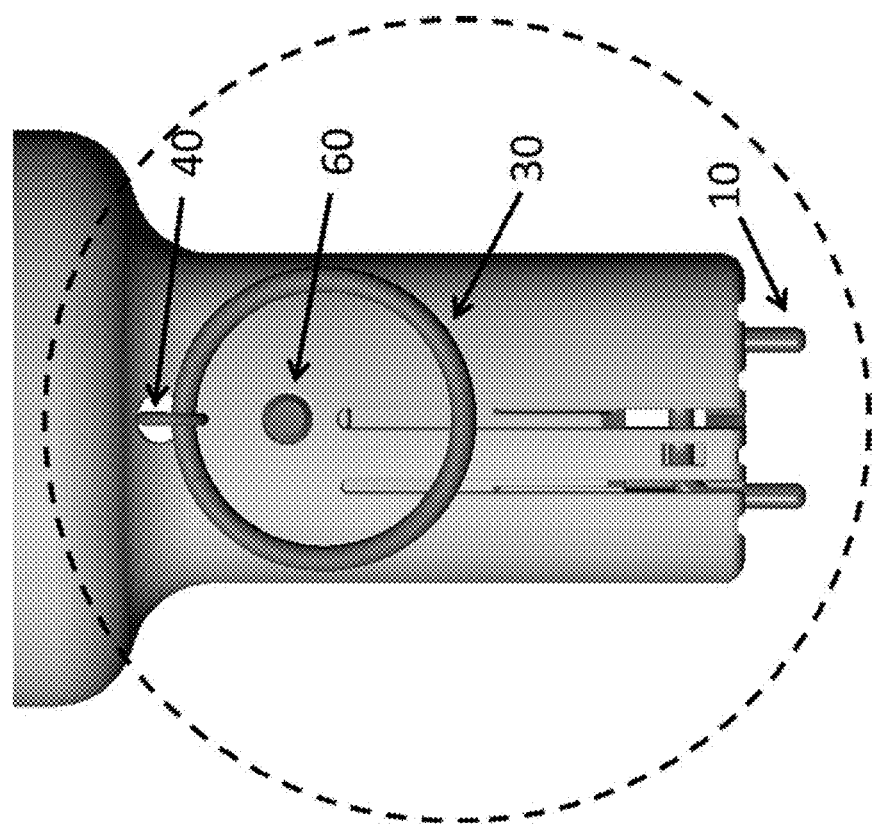
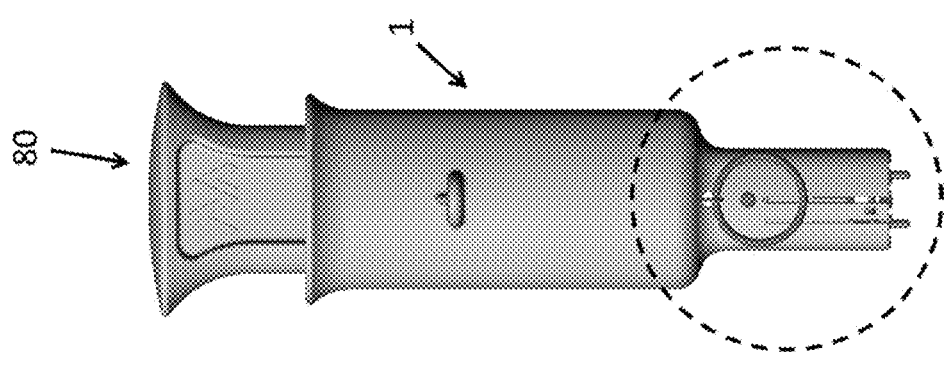
FIG. 13B
FIG. 13A

BONE STAPLE EXTRUSION INSTRUMENT AND METHOD OF USE AND MANUFACTURING

CROSS-REFERENCE TO RELATED PATENT APPLICATIONS

This application claims priority to U.S. Patent Appl. Ser. No. 61/759,327, filed Jan. 31, 2014, entitled "Bone Staple Extrusion Instrument and Method of Use and Manufacturing." This application further claims priority to: (a) U.S. patent application Ser. No. 13/192,162; (b) U.S. patent application Ser. No. 13/192,177 (now abandoned); (c) U.S. patent application Ser. No. 13/192,186 (now U.S. Pat. No. 9,017,331), and (d) U.S. patent application Ser. No. 13/192, 198 (now U.S. Pat. No. 9,339,268). Each of the foregoing patent applications was filed on Jul. 27, 2011, is entitled "Bone Staple, Instrument and Method of Use And Manufacturing," and is commonly owned by the owner of the present invention. This application is related to International Patent Application No. PCT/US12/48,539 filed on Jul. 27, 2012, entitled "Bone Staple, Instrument and Method of Use And Manufacturing" (the PCT '539 Patent Application"), which claimed priority to each of (a) U.S. patent application Ser. No. 13/192,162; (b) U.S. patent application Ser. No. 13/192,177; (c) U.S. patent application Ser. No. 13/192,186' and (d) U.S. patent application Ser. No. 13/192,198. The foregoing patent applications are hereby incorporated herein by reference in their entirety for all purposes.

TECHNICAL FIELD

This application relates to bone staple extrusion instruments used for fixation of bone and soft tissue of the musculoskeletal system and the methods for their use and manufacture. More specifically, the bone staple extrusion instruments are used for insertion of staples into bones, which staples change shape through their metallurgic properties and by their release from the bone staple extrusion instruments. In some embodiments, the bone staples pull together and compress bone once released from the bone staple extrusion instruments. In other embodiments, the staples push outward to place the bones in tension once released from the bone staple extrusion instrument.

BACKGROUND

Bone staples have been in clinical use for decades. These important bone fixation devices have evolved from rigid stainless steel or cobalt-chromium U-shaped implants to staples that could be manipulated to compress two adjacent bone segments.

The early rigid staples were commonly hammered into bone where the more modern devices are implanted in drilled holes and use heat or mechanical means to cause the staple to change shape and pull together and in some designs compress the bony segments. Bone staple technology used to pull bone together includes: 1) staples that are bent by an instrument: BENDABLE STAPLES, 2) heat sensitive shape memory alloy staples: MEMORY STAPLES, and 3) mechanical elastic bone staples: ELASTIC STAPLES.

The staple embodiments of this invention have advantages over the prior art because it stores mechanical energy and imparts that energy to bone through shape change and predictable bone-to-bone compression. The staple embodiments of this invention pull together and compress bone to promote healing. The prior art implants may change shape or be caused to change shape but do not pull together and compress bone with a predicable amount of shape change and compression force.

Instruments, to implant staples into bone, complement the staple's method of action. BENDABLE STAPLES use pliers, forceps, and complex instruments to apply the bending force. MEMORY STAPLES must be kept cold for body temperature heating or use an electrical resistive heating instrument to transition their crystalline structure from martensitic to austenitic. Prior ELASTIC STAPLES use pliers, hooks, forceps, and complex instruments to stretch and hold their shape while being implanted. These designs cause the surgeon to need to manipulate the implant while trying to implant it in bone. Thus these implants were difficult to implant or required complex expensive instruments thus impeding their use.

As will be clear in the following detailed description of the prior art, the embodiments illustrated of the subject invention overcome the prior art deficiencies in ease of use, manufacturing, mode of operation, strength, cost and allows hospital procedures that limit disease transmission.

Bendable Staples

Bendable staple designs use an instrument to bend the staple to facilitate placement, retention and bone movement. These designs can be bent to pull the bone together but partially spring open and provide no bone-to-bone compression.

Murray, in U.S. Pat. No. 3,960,147 uses pliers to squeeze the bridge of a staple to toe it in to enhance fixation. Weaver, in U.S. Pat. No. 4,444,181 uses a dual bridge staple and pliers to decrease the distance between the legs of a staple when the dual bridge is squeezed together. Garner, in U.S. Pat. No. 4,841,960 uses pliers to squeeze the bridge of a staple to bring the legs together.

Groiso, in U.S. Pat. No. 5,853,414, U.S. Pat. No. 5,449, 359 and U.S. Pat. No. 7,635,367 uses pliers to bend a dual bridge titanium alloy or stainless steel staple, widening the bridge to shorten the distance between the legs and narrowing the bridge to lengthen the leg distance. Groiso calls this bending or permanent deformation "elastic" behavior when in fact this bending is mostly plastic deformation. Stainless steel and titanium alloy's elastic behavior is characterized by the 2% offset yield strength. Thus when bent with pliers or forceps the material undergoes both elastic (recoverable) and plastic (permanent) deformation. This elastic behavior under strain causes the staple to partially return to its pre-bent shape. The staple legs thus partially "spring back" and thus this type of staple does not cause bone segment compression once the pliers are no longer bending the staple. Groiso, in published continuation application Ser. No. 11/197,174 adds nitinol and shape memory features to his staple.

Hardengen, in published application Ser. No. 10/940,396 also uses pliers and in its continuation application Ser. No. 12/582,210 Hardengen describes shape memory metal to widen the dual bridge screw plate of its parent application. Hardengen's invention is embodied in the Charlotte Staple and described in the Wright Medical, Charlotte Foot and Ankle Fixation System, page 4 and 6 document number SO 040-105 Rev. 04.06

These bendable implants bring the bone together, allow it to partially spring apart and provide no compression once the instrument is removed. They store no mechanical energy. They cannot continue to change shape to pull the bone together if a gap occurs during healing. This gap can result in delayed or non-healing. Consequently, with this impaired healing observation clinical demand for this type of bone staple has decreased. The embodiments of the subject invention of this patent overcomes the deficiencies of the bendable staples by not requiring manipulation of the implant and by storing shape changing elastic mechanical energy that continuously applies force to bone to pull it together and compress.

Memory Staples

Memory staples fabricated from the nickel-titanium alloy, nitinol, exhibit a shape memory effect when heated within their martensitic and austenitic microstructure temperature transition range. A U-shaped implant can be fabricated so that it returns to a predetermined final shape. Traditionally these implants have parallel legs and then when heated the legs change shape at the corners of the U-shaped bridge to bring the tips of the legs together so as to lock in bone and in some designs create bony compression. The bridge of these staples often have a geometry capable of changing shape so it can be shortened to provide further bony compression. These heat sensitive implants can have their shape change temperature varied by changes in their composition, residual stress in the material and heat treatment.

Mai, U.S. Pat. No. 5,246,443 used a martensitic to austenitic transition temperature of 10° C. to 15° C. and described a number of bone staples and plates and relied on body heat to initiate the transformation. Mai, in U.S. Pat. No. 5,474,557 presented a temperature transition range of −20° C. to 70° C. of which temperatures over 37° C. exceed body temperature and further described other staples, plates and clips. Bertolet, in U.S. Pat. No. 5,779,707 introduced shape changing holes and slots to shorten the bridge section of plates, staples and clips but again used martensitic to austenitic transformations at body temperature to affect their shape. Ogilvie, U.S. Pat. No. 6,325,805 and U.S. Pat. No. 6,773,437 expanded the use of body temperature staples for correction of spinal deformity.

These heat sensitive staples that rely on microstructure transition are problematic because during implantation the staple is in its mechanically soft martensitic state and commonly deform inappropriately with the impaction of surgical placement. Furthermore, during shipping, costly strategies must be implemented to keep environmental heating from causing the staple to change shape prior to implantation. Finally, a heating strategy must be used to activate the implant.

Originally heat sensitive nitinol staples were activated with the temperature of the human body, approximately 37° C. This strategy and implant formulation caused critical issues by changing shape and applying bone fixation forces only after the surgical wound had been closed and allowed to warm to normal body temperature. This post surgery shape change was reported to cause deformity and fracture. This style of nitinol staple was further inconvenient in its use because the transition temperature began at below room temperature thus these implants were changing shape while being implanted by the surgeon. Strategies such as keeping the staple on dry ice were used to partially overcome this issue but it added cost and the surgeon had to work quickly in procedures where deliberate and detailed technique was required.

The body temperature nitinol staples are further described in Biopro, Inc.'s Memory Staple Brochure, and Depuy Inc.'s Memory Staple Brochure. The review of the prior art patent, technical and sales literature it is clear that the cost, inconvenience and risk of use of body temperature staples have impeded clinical adoption due to complications.

Staples that changed shape at temperatures above body temperature were developed to avoid the implant changing shape during surgery and to provide shape change and force control of the implant. Fox, U.S. Pat. No. 7,240,677 used a controlled amount of electrical current passed through the metal to resistively heat staples above body temperature to convert the martensitic crystalline structure to austenitic. Fox, U.S. Pat. No. 7,240,677 set the transition temperature of the implant and the resistive current heating level so that this elevated temperature implant was below the heat level of tissue injury. This invention is further illustrated in the BioMedical Enterprises, Inc., BME_OSStaple_sell_sheet_B. Flot, U.S. Pat. Nos. 6,323,461 and 6,268,589 used electrical current to heat the staple but had no ability to control the extent of staple shape change.

Though Fox's, U.S. Pat. No. 7,240,677 elevated temperature staple heating strategies have seen extensive clinical use, this style and the body temperature heated implants are deficient due to variation in bone fixation force due to environmental heating or cooling and are soft in their mechanical properties during implantation. These issues and the requirement to have dry ice or an electrical bipolar heating unit have limited the clinical adoption of elevated temperature staples.

The embodiments of the subject invention of this patent overcomes the deficiencies of the memory staples such as 1) requiring heating or cooling, 2) having a temperature dependent fixation force, 3) requiring ancillary equipment to manipulate the implant, 4) being implanted in the soft martensitic phase, 5) requiring an expensive multiple step manufacturing process to set both the staple shape and transition temperatures, and 6) others that become more clear in the review of the embodiments of the subject invention.

Elastic Staples

Mohr, U.S. Pat. No. 3,939,828 first introduced the use of elastic properties of stainless steel for a bone staple. This invention the Osteoclasp™ was an S-shaped bridge staple with convergent legs. (A staple has a "convergent" shape when the legs of the staple are in a convergent orientation, as opposed to a substantially parallel orientation or a divergent orientation). In use, one leg was placed in an angled drill hole and the other pulled with a hook until it could be inserted in a second drill hole. The elastic spring-back of the stainless steel pulled the bone together and caused bone-to-bone compression. The legs are not manipulated to converge and compress, though Mohr's angled drill holes impede staple extrusion from bone. The clinical use of the Mohr staple has been long discontinued due to difficulty in stretching the bridge during placement and the frequency of having the staple unexpectedly released from the hook and spring from the surgical field.

Allen, in U.S. Pat. No. 6,348,054, U.S. Pat. No. 6,059,787 and U.S. Pat. No. 6,783,531 used a bowed bridge shaped staple and a complex instrument to pull the legs of the staple apart to straighten the bowed bridge while impacting the staple legs into bone. The elastic spring back of the bowed bridge staple pulled the bone together and caused bone-to-bone compression. Allen does not manipulate the legs and thus the parallel legs do not converge and resist extrusion from the bony drill holes. The cost of the instrument is high and no commercial embodiment of this invention is known.

Jervis, in U.S. Pat. Nos. 5,067,957 and 4,665,906 introduced the use of nitinol formulated to fully transition from stress induced martensite to austenite at body temperature for the fabrication of bone staples, plates and rods. Monassevitch, in U.S. Pat. No. 6,685,708 teaches the use of pliers or forceps on nitinol staples to plastically change the distance between the legs and allow the martensitic to austenitic crystalline structure of nitinol to move the legs back to the original distance once released. This invention requires the surgeon to change the shape of the staple during implantation, has high fixation force variation and does not provide a feature to impact the staple into bone. The shape recovery causes the staple bridge to shorten but does not angle the legs to resist extrusion from the bony drill holes. Monassevitch, claims a hand operated instrument for manipulating the staple and teaches that the staple must be cold and in its soft martensitic state so that the hand operated instrument has enough force to deform the staple. This is a sufficient deficiency because, the hand deforming is not precise, the staple must be sterile and made cold before deforming and the implant is soft when implanted and thus may bend with the impaction of placement in bone.

Memometal, Inc. sells an elastic staple, the EasyClip™. The EasyClip™ has a straight bridge and convergent legs. Pliers are used to pry the legs apart so that they can be inserted in predrilled holes. When the pliers release the staple legs they can swing in if the drill holes are loose or the bone is soft. The EasyClip™ cannot pull together and compress bone because the bridge is straight and constrained in the drill holes. This straight and rigid bridge defeats compression. The inward movement of the legs only tightens the legs in the holes to impede extrusion of the staple from the bone holes.

The simultaneous requirement for the surgeon to open the staple legs and insert the implant into bone is surgically difficult in many procedures, and for the other reasons noted above, have limited the clinical use of this implant. Memometal, Inc.'s Easy Clip Brochure further illustrates the deficiencies of these staple implants that are elastic and manipulated with pliers, complex instruments, forceps and hooks for stretching. The Easy Clip is described as having super elastic properties and there is no indication that the opening of the legs with pliers creates stress induced martensite in the staple to leg corners and certainly not in the straight bridge.

Though Jervis describes staples and many other medical implant applications the geometry of the staple is not described. Monassevitch presents a Z-shaped bridge that can be compressed into an S-shape but teaches away from legs angled in relation to the bridge and promotes a non-shape changing leg to bridge corner. The Easy Clip has a straight bridge and though its legs can deflect inwards to tighten in the hole this device cannot pull together and compress. This prior art stress induced martensite or super elastic implants have not taken advantage of the geometric leverage provided by the O-shaped or S-shaped bridge at contracting or lengthening or the bridge to leg corner to enhance the amount the staple can pull together and compress two structures. The prior art teaches elastic behavior but teach away from a staple geometry that creates optimal shape change and compression. Consequently, in use these implants have significant disadvantages compared to the embodiments of the subject invention.

The embodiments of the subject invention of this patent overcomes the deficiencies of the prior elastic staples such as 1) requiring the surgeon to stretch the staple to place it in bone, 2) designs that cannot contract their bridge, 3) requiring expensive ancillary equipment such as staple guns to manipulate the implant, 4) requiring the surgeon to change the staple shape with pliers, forceps or other hand operated instruments, 5) cooling of the implant prior to opening for placement, 6) designs that cannot simultaneously provide in their bridge and legs geometric leverage to pull together and compress bone, and 6) others deficiencies that will become more clear in the review of the embodiments of the subject invention.

Instrument and Staple Implant Devices and Methods

Shapiro, U.S. Pat. No. 4,414,967 describes a pneumatic staple gun that combined with a staple cartridge violently impacted staples into bone. The staple's legs were divergent so that they pull bone together when inserted. (A staple has a "divergent" shape when the legs of the staple are in a divergent orientation, as opposed to a substantially parallel orientation or a conversion orientation). This implant did not change shape to pull together and compress bone. The instrument was complex, expensive and in aged porous bone sometimes caused bone fracture during staple insertion.

Assell, U.S. Pat. No. 4,527,726 and Bent, U.S. Pat. No. 4,540,110, as did Shapiro U.S. Pat. No. 4,414,967, both illustrated an automatic stapler that forces a staple down a channel with significant energy to impact this implant into bone. These staples do not store mechanical energy or change shape and thus the staples of his system cannot pull together and compress bone. The convenience of these systems is overcome by the high cost, complicated design of the staple gun, and difficulty in cleaning and sterilizing the stapler for repeated patient use.

McHarrie, U.S. Pat. No. 4,415,111 proposed a locator tube having a staple in a slot and a cooperating punch to push the staple from the tube into bone. McHarrie's invention cannot be used with shape changing staples because it does not constrain the staple legs from swinging in or the bridge from shortening. Consequently, the staples of this system do not change shape to pull together and compress bone. Pratt, U.S. Pat. No. 4,438,769, used a simple system to hold the staple bridge in a grasping driver that used a threaded coupler to lock the staple. This system supported the staple during hammer insertion into bone and through its geometry may urge bone together. The staple did not change shape to pull together and compress bone because the system required rigid staples to withstand the bone impaction forces.

That foregoing discussion illustrates the deficiencies of the prior art and the lack of a simple shape changing staple instrument for staple implantation consistent with the demands of surgery. In the discussion of the embodiments of the subject invention, the benefits of the present invention will be realized as a simple, reliable, low cost solution to present an elastic energy storing shape changing staple to bone and releasing the staple so that it can pull together (or pull apart) and compress bone even in the presence of gaps that can form during bone healing.

SUMMARY OF THE INVENTION

The embodiments of the subject invention are an improved bone staple instruments for applying staples that store recoverable mechanical energy in its structure and changes shape when released from the instrument (such as by pulling together and compressing the bone fixation interface).

In general, in one aspect, the invention features a bone staple extrusion instrument that includes a cartridge that can restrain a bone staple such that the bone is maintained in a first position. The bone staple is operable for spontaneously moving to a second position when released from the cartridge. The bone staple is operable for moving from the first position to the second position without substantial plastic deformation of the bone staple. The bone staple comprises a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge.

Implementations of the invention can include one or more of the following features:

The movable actuator can include a lever movably integrated into the cartridge.

The movable actuator can include a wire lever.

The movable actuator can include a wire ring that can be separated from the other portions of the cartridge.

The extruder can be operable for moving the movable actuator causing the bone staple to be extruded from the cartridge.

The extruder can be operable for directly contacting the movable actuator.

The extruder can be operable for directly contacting the bone staple and the bone staple is operable for directly contacting the movable actuator.

The bone staple extrusion instrument can further include the bone staple, which is restrained in the first position by the cartridge.

The bone staple can include memory shape metal.

The bone staple can include stress induced memory shape metal in the martensite phase.

The bone staple can have stress induced forces that are being restrained by the cartridge, which stress induced forces are operable for spontaneously moving the bone staple from the first position to the second position when released from the cartridge.

The bone staple can include stress restrained memory shape metal in the martensite phase.

The bone staple can have has stress induced forces that are being restrained by the cartridge, which stress induced forces are operable for spontaneously moving the bone staple from the first position to the second position when released from the cartridge.

The cartridge can further include a lock pin assembly operatively connected to the movable actuator.

The lock pin assembly can include a lock pin and a lock ring.

In general, in another aspect, the invention features a kit including a bone staple extrusion instrument. The bone staple extrusion instrument includes a bone staple. The bone staple extrusion instrument further includes a cartridge that can restrain the bone staple such that the bone staple is maintained in a first position. The bone staple is restrained in the first position by the cartridge. The bone staple is operable for spontaneously moving to a second position when released from the cartridge. The bone staple is operable for moving from the first position to the second position without substantial plastic deformation of the bone staple. The bone staple includes a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge. The kit further includes a drill guide corresponding to the bone staple when in the first position.

Implementations of the invention can include one or more of the following features:

The bone staple extrusion instrument and drill guide can be pre-sterilized.

The kit further includes a package in which the bone staple extrusion instrument and drill guide are contained and maintained sterilely.

The kit can further include a drill bit corresponding to the bone staple and the drill guide.

The kit can include a tray that holds the bone staple extrusion instrument and the drill guide.

In general, in another aspect, the invention features a pre-sterilized kit including a bone staple extrusion instrument. The bone staple extrusion instrument includes a bone staple. The bone staple extrusion instrument further includes a cartridge that can restrain the bone staple such that the bone staple is maintained in a first position. The bone staple is restrained in the first position by the cartridge. The bone staple is operable for spontaneously moving to a second position when released from the cartridge. The bone staple is operable for moving from the first position to the second position without substantial plastic deformation of the bone staple. The bone staple includes a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge. The bone staple extrusion instrument is sterilized. The kit further includes a package in which the bone staple extrusion instrument is contained and maintained sterilely.

In general, in another aspect, the invention features a method of implanting a staple into bone. The method includes selecting a bone staple extrusion instrument. The bone staple extrusion instrument includes a bone staple. The bone staple extrusion instrument further includes a cartridge that can restrain the bone staple such that the bone staple is maintained in a first position. The bone staple is restrained in the first position by the cartridge. The bone staple is operable for spontaneously moving to a second position when released from the cartridge. The bone staple is operable for moving from the first position to the second position without substantial plastic deformation of the bone staple. The bone staple includes a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge. The method further includes lining up the bone staple of the bone staple extrusion instrument with the bone in which the bone staple is to be implanted. The method further includes moving the extruder relative to the cartridge of the bone staple instrument to cause the bone staple to be extruded from the cartridge and into the bone. The bone staple spontaneously moves toward the second position when extruded from the cartridge.

Implementations of the invention can include one or more of the following features:

The movable actuator of the bone staple extrusion instrument can include a lever movably integrated into the cartridge. The cartridge can include lever face angles designed so that the bone staple moves upon the lever face angles as the bone staple is being extruded from the cartridge and moving the second position.

The method further includes drilling holes in the bone using a drill guide corresponding to the bone staple.

In general, in another aspect, the invention features a method of loading a bone staple into a bone staple extrusion instrument. The method includes selecting a bone staple. The method further includes selecting a bone staple extrusion instrument. The bone staple extrusion instrument includes a cartridge that can restrain the bone staple such that the bone staple is maintained in a first position. The bone staple is operable for spontaneously moving to a second position when released from the cartridge. The bone staple is operable for moving from the first position to the second position without substantial plastic deformation of the bone staple. The bone staple includes a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge. The bone staple extrusion instrument is operable for restraining the bone staple in the first position. The staple is in the second position. The method further includes mechanically moving the staple to the first position. The method further includes loading the staple into the cartridge such that the cartridge restrains the staple in the first position.

In general, in another aspect, the invention features a method of loading a staple into a bone staple extrusion instrument. The method includes selecting a bone staple. The bone staple includes memory shape metal and is at a temperature below room temperature. The method further includes selecting a bone staple extrusion instrument. The bone staple extrusion instrument includes a cartridge that can restrain the bone staple such that the bone staple is maintained in a first position. The bone staple is operable for spontaneously moving to a second position when released from the cartridge. The bone staple is operable for moving from the first position to the second position without substantial plastic deformation of the bone staple. The bone staple includes a bridge and legs. The bone staple is in the first position when the legs of the bone staple are substantially parallel. The bone staple is in the second position when the legs of the bone staple are substantially non-parallel. The cartridge has a movable actuator that can restrain the bone staple in the first position. The bone staple extrusion instrument further includes an extruder operatively connected to the cartridge. The extruder is operable for moving relative to the cartridge to cause extrusion from the cartridge of the bone staple being restrained by the cartridge. The bone staple extrusion instrument is operable for restraining the bone staple in the first position. The bone staple is in the second position at the temperature below room temperature. The bone staple is operable to move to the first position at room temperature. The method further includes loading the bone staple into the cartridge while the staple is in the second position. The method further includes allowing the bone staple to warm to room temperature such that the bone staple extrusion instrument is restraining the staple from moving from the first position to the second position.

DESCRIPTION OF DRAWINGS

FIG. 3A: The staple extrusion instrument of FIG. 1 with the tip portion circled.

FIG. 3B: A magnified view of the tip portion of the staple extrusion instrument circled in FIG. 3A.

FIGS. 4A-4B: Perspective views of the portion of the staple extrusion instrument of FIG. 1 focusing upon the portion holding staple 10.

FIG. 13A: The staple extrusion instrument of FIG. 11 with the tip portion circled.

FIG. 13B: A magnified view of the tip portion of the staple extrusion instrument circled in FIG. 13A.

REFERENCE NUMERALS

Figure 1:
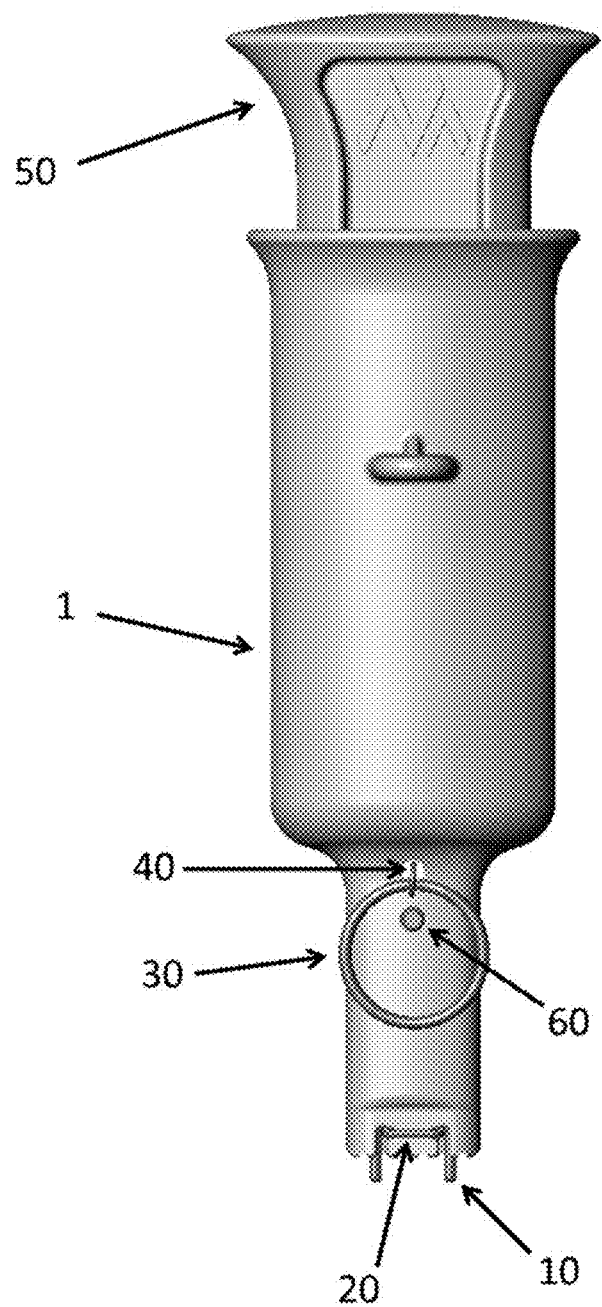
FIG. 1: A staple extrusion instrument in which the cartridge 1 holds the staple 10 in position until extruded from the cartridge 1. This embodiment of the staple extrusion instrument utilizes a wire lever 20 component to the cartridge that disengages the staple 10 from the cartridge 1 thereby transferring the staple force from the cartridge 1 to the structure into which the staple 10 is inserted.

1 Cartridge.
3 Cartridge lever.
5 Lever face angles.
7 Lever bumps.
8 Lever ramp.
9 Extruder face.
10 Staple.
20 Cartridge wire levers.
30 Lock pin ring.
40 Lock pin.
50 Extruder.
60 Slide pin.
70 Release wire ring.
75 Cartridge bumps.
80 Extruder.
100 Drill bit.
110 Drill guide.
120 Drill hole locating pins.
130 Bone fixation wires.
140 Package.

DETAILED DESCRIPTION

The embodiments of the subject invention are staple extrusion instruments (or bone staple extrusion instruments) that are each utilized for retaining and then implanting a staple with a plurality of legs, commonly in a U- or table-shaped configuration where the U-shaped has two legs and the table-shaped has three or more legs. All staple styles independent of the number of legs have a bridge that joins the plurality of legs. The particular staple extrusion instrument is designed to receive and restrain a corresponding configuration of the staple that is to be retained and implanted using that staple extrusion instrument.

Staples

As discussed and described herein, embodiments of the present inventions include staple extrusion instruments and methods of use to implant staples in which the staples are able to move between two shapes. Generally, one shape is a "parallel" shape, and the other shape is a "non-parallel" shape. A staple has a "parallel" shape when the legs of the staple are in a substantially parallel orientation, as opposed to a convergent orientation or a divergent orientation. A staple has a "non-parallel" shape when the legs of the staple are not in a substantially parallel orientation, i.e., the staple is in a convergent orientation or a divergent orientation.

When a staple is a "convergent staple," the staple is able to move between a parallel shape (i.e., the legs of the convergent staple are substantially parallel) and a convergent shape (i.e., the legs of the staple are in a convergent orientation). Since the non-parallel configuration of a convergent staple has converging staple legs, the non-parallel shape of a convergent staple is also referred to as the "closed" shape of a convergent staple. Likewise, the parallel shape of a convergent staple is also referred to as the "open" shape of a convergent staple.

When a staple is a "divergent" staple, the staple is able to move between a parallel shape (i.e., the legs of the divergent staple are substantially parallel) and a divergent shape (i.e., the legs of the divergent staple are in a divergent orientation). Since the non-parallel configuration of a divergent staple has diverging staple legs, the non-parallel shape of a convergent staple is also referred to as the "open" shape of a divergent staple. Likewise, the parallel shape of a divergent staple is also referred to as the "closed" shape of a divergent staple.

Whether a staple is in an open shape or a closed shape depends upon the orientation of staple legs and whether the staple is a convergent staple or a divergent staple. The "open" shape of a convergent staple and the "closed" shape of a divergent staple are the circumstances in which the legs of the staple have a substantially parallel orientation. A convergent staple thus moves from its open shape to its closed shape when the legs of the convergent staple move from the substantially parallel orientation to a convergent orientation. The divergent staple thus moves from its closed shape to its open shape when the legs of the divergent staple move the substantially parallel orientation to a divergent orientation.

The staple embodiments of the subject invention are designed to internally store mechanical energy in its structure and expend energy to change the shape of the staple or apply force to bone. Mechanical energy is stored in the metal matrix and is recoverable. Generally, the mechanical energy is stored when the staple embodiments are in a parallel shape (i.e., an open shaped convergent staple or a closed shaped divergent staple), and the mechanical energy is recovered when then the staple embodiments move toward their non-parallel shape (i.e., a closed shaped convergent staple or an open shaped divergent staple).

In metals that exhibit linear elastic deformation the energy is stored as molecular bonds are strained but not broken. Nitinol deformation strains and rearranges molecular bonds to store mechanical energy. This energy is recovered when the metal grossly changes shape as a result of its crystalline structure transitions from martensite to austenite. Though table-shaped and other shapes of staples with multiple legs can be used in embodiments of the subject invention, the S-shaped staple will be used by example to illustrate, but not limit, embodiments of the subject invention.

Representative staples that can be used in embodiments of the present invention include S-shaped staples in their closed first shape (closed with the bridge contracted and legs deflected together, i.e., the S-shaped staple embodiment is in a convergent shape). Such a staple can be cut from a rod of material in its closed first shape using three dimensional cutting techniques such as, but not limited to, milling, electro-discharge, water jet, or laser machining.

The staple has a bridge and legs (with leg tips at the end of each leg). For an S-shaped staple (convergent), the bridge is undulated and contracted and the legs are angled together (when in its first closed shape). The leg tips converge toward each other. The staples can be rounded for insertion into a drill hole or sharp for impaction into bone.

The S-shaped staple (convergent) is in an open second shape when its legs are parallel and its bridge is extended (its implanted configuration). In this open second shape the staple's undulated bridge is lengthened and the staple legs have been strained, predominantly at the corners adjoining the bridge so that each leg is parallel with one another.

Staples other than S-shaped staples can be used in embodiment of the present inventions, such as O-shaped staples using an O-shaped bridge. For a convergent O-shaped staple, the staple is in a closed first shape when the O-shaped bridge is contracted and the legs of the staple are deflected together when cut from a bar. Such staple is in its second open shape when O-shaped bridge is extended and the legs are parallel (the implanted shape). When released in bone, the stored mechanical energy in a convergent O-shaped staple in the second position causes the legs of the staple to move towards one another and the bridge to contract to pull together and compress bone.

Prior art, shape changing nitinol staples were cut from wire, bent and heat treated in multiple steps to form a O-shape bridge-to-leg configuration and S-shaped bridge. After these steps the prior art staples are then heat treated a final time to set the transition temperature to match the needs of a body temperature or electrically heated nitinol bone staple.

The manufacturing methods of embodiments of the subject invention for shape changing staples significantly simplifies manufacturing, reduces cost and minimizes staple performance variation over the prior art. Manufacturing of embodiments of the staple requires two steps. Step 1: cut the staple in its closed first shape and Step 2: simultaneously strain the legs to become the parallel legs and the S-shaped bridge to become an elongated S-shaped bridge. This straining stores mechanical energy in the staple's metal matrix during manufacturing.

Staple Cartridge

This energy stored when the staple is in its second open shape wants to spontaneously return the staple geometry to the first closed shape if released. To maintain the staple in its second open shape during shipping, handling and implantation the subject staple is retained in an extrusion cartridge. The staple is placed in the cartridge during manufacturing.

In some embodiments, to place the staple in the cartridge, the staple is strained into the second open shape (for convergent staples) and inserted into the S-shaped or O-shaped extrusion channel. Alternatively, the extrusion channel can receive the convergent staple in a first closed shape and when extruded through the cartridge the staple is acted on by features in the cartridge channel that manipulate and strain the staple to a second open shape prior to implantation.

For example, an S-shaped staple storage, sterilization, retention and extrusion cartridge can be utilized (which is shown in FIG. 4 of the PCT '539 patent Application). Such a cartridge has an internal shape to hold the staple in its second open shape S-shaped bridge staple configuration, a retention tab to hold the staple in the cartridge, and a cam to release the staple when extruded by the staple insertion instrument.

Figure 5:
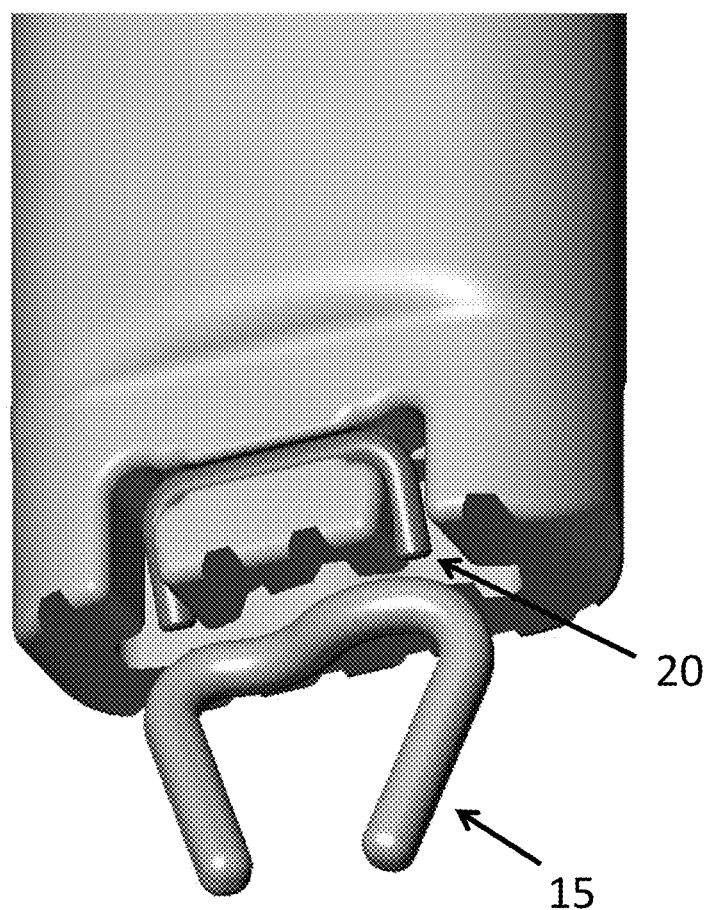
FIG. 5: A perspective view of the portion of the staple extrusion instrument illustrated in FIG. 4B after staple 10 has been extruded and changed shape to the configuration of staple 15.

Also, for example, an O-shaped staple storage, sterilization, retention and extrusion cartridge can be utilized (which is shown in FIG. 5 of the PCT '539 patent Application). Such a cartridge has an internal shape to hold or cause the staple to strain to its second open shape O-shaped bridge configuration. The cartridge can have a retention tab to retain the staple in the cartridge, and a cam to release the staple when extruded by the staple extrusion instrument.

Cartridge retention tabs and release cams may not be required for high force staples where wall pressure of the staple against the cartridge channel or is sufficiently high to create friction. For this embodiment, the cartridge must create enough staple-to-channel friction so that the extrusion forces are not excessive but the retention of the staple in the cartridge is sufficient.

FIG. 6A of the PCT '539 patent Application shows a schematic of an S-shaped staple in a cartridge with elongated bridge and parallel legs when retained in the cartridge and below after extrusion from the cartridge in its recovered first closed shape with contracted bridge and inward deflected legs. FIG. 6A of the PCT '539 patent Application shows a schematic of an O-shaped staple shown in the open second shape with elongated bridge and parallel legs while retained within the cartridge and below after extrusion of the O-shaped staple from the cartridge with its bridge contracted and its legs deflected inward.

Such a staple can be extruded from the cartridge with a separate reusable extrusion instrument or integral disposable extrusion instrument. This allows the clinical product to be part of a hospital sterilized tray or a pre-sterilized fully disposable procedure specific kit.

The reusable staple instrument can have an extrusion mandrel with an S-shaped face (or other shaped face) that matches the bridge of the staple and tab lock slots. When the instrument's extrusion mandrel is advanced through the cartridge channel, it can simultaneously disengage the staple retention tab and extrude the staple from the cartridge into bone. The O-shaped bridge staple and cartridge uses an O-shaped extrusion mandrel.

To support the surgeon and treat the patient, several reusable staple instruments can be placed in a surgical tray with tens of cartridges each containing a staple and ancillary instruments such as drill bits, drill guides, mallets, forceps, and impactor. This surgical tray is reusable, hospital cleaned and sterilized and replenished as implants are used or instruments damaged. These types of all-inclusive surgical trays are required for large surgical procedures involving multiple implants.

This reusable implant and instrument tray configuration is common to the market and prior art. Today's marketed staple systems all have at least one element that is reused and must be cleaned and sterilized by the hospital. This increases the cost of use and frequency of complication. Incomplete cleaning or sterilization can cause intra-patient disease transmission. This is most commonly an infection but can become of grave concern when the infection is antibiotic resistant or viral.

To reduce hospital handling cost and minimize the incidence of hospital related infections embodiments of the subject invention can be built with a disposable staple instrument combined with an integral cartridge (such as an S-shaped staple cartridge). This embodiment and other embodiments can be delivered to the hospital in a quality controlled sterile package.

The integral instrument has an extrusion mandrel with an S-shaped face that matches the bridge of the staple and is assembled with the S-shaped bridge staple of which both are within cartridge. When the instrument's extrusion mandrel is advanced through the cartridge channel it simultaneously disengages the staple retention tab of the cartridge and extrudes the staple from the cartridge and into bone. The O-shaped staple and cartridge uses an O-shaped extrusion mandrel.

This pre-sterilized combination instrument, cartridge and implant can be packaged with a drill and drill guide so that the medical procedure kit fully supports the surgical technique. Hospital costs savings are achieved because there is no hospital cleaning or sterilization required and the patients and hospital benefit from fewer infections and patient complications.

Wire Lever Cartridge

FIGS. 1-2, 3A-3B, 4A-4B, and 5-6 are illustrations of an embodiment of the present invention. In the embodiment of FIG. 1, the staple extrusion instrument has a cartridge 1 that can be hand held and that holds staple 10 in position until extruded from the cartridge 1. Cartridge 1 also holds the other elements of the staple extrusion instrument. An extruder 50 fits within the cartridge 1 and can be moved relative to the cartridge 1. In the orientation of the FIG. 1 (with the extruder 50 at the top of the staple extrusion instrument), the extruder 50 can be moved downward. In this embodiment, extruder 50 is a hand operated plunger that pushes the staple 10 which acts on the mechanism (cartridge lever 20) to release and implant the staple 10. Cartridge lever 20 is one or more levers (such as a metal lever as shown or a lever made from another material, like plastic) that hold the staple 10 until swung down by the movement of the staple 10 due to the contact of the advancing extruder 50. As shown in FIG. 1, staple 10 is a staple having an S-shape bridge extended and the legs parallel storing elastic energy. While this staple shape is utilized throughout the drawings, the design of the staple extrusion instrument can be adjusted for alternative staple designs. Furthermore, for the purposes of this description, Applicant will refer to staple 10 as having the characteristics of a convergent staple (i.e., when released, the legs of staple 10 will move together to a convergent orientation).

Cartridge 1 and extruder 50 can each be made of various materials, such as metal or plastic. In some embodiments, cartridge 1 and extruder 50 are both made of plastics, such as thermoplastics including but not limited to polycarbonate, PVC, Teflon, polyethylene, and combinations thereof.

The staple extrusion instrument shown in FIG. 1 also has a lock pin assembly that includes a lock ping ring 30 and a lock pin 40 (made of metal and/or plastic). The lock pin assembly is utilized to keeps the extruder 50 from being able to be moved in a manner that would inadvertently release staple 10. I.e., the lock pin assembly (and more specifically the lock pin 40) must be removed before the stable 10 can be extruded from the staple extrusion instrument. Lock ring 30 is a ring connected to the lock pin 40 that facilitates grasping and removal of the lock pin 40.

The staple extrusion instrument shown in FIG. 1 also has a slide pin 60 (made of metal and/or plastic) that is a permanent pin that allows sliding of the extruder 50 in the cartridge 1 but keeps the extruder 50 and cartridge 1 from separating.

Figure 2:
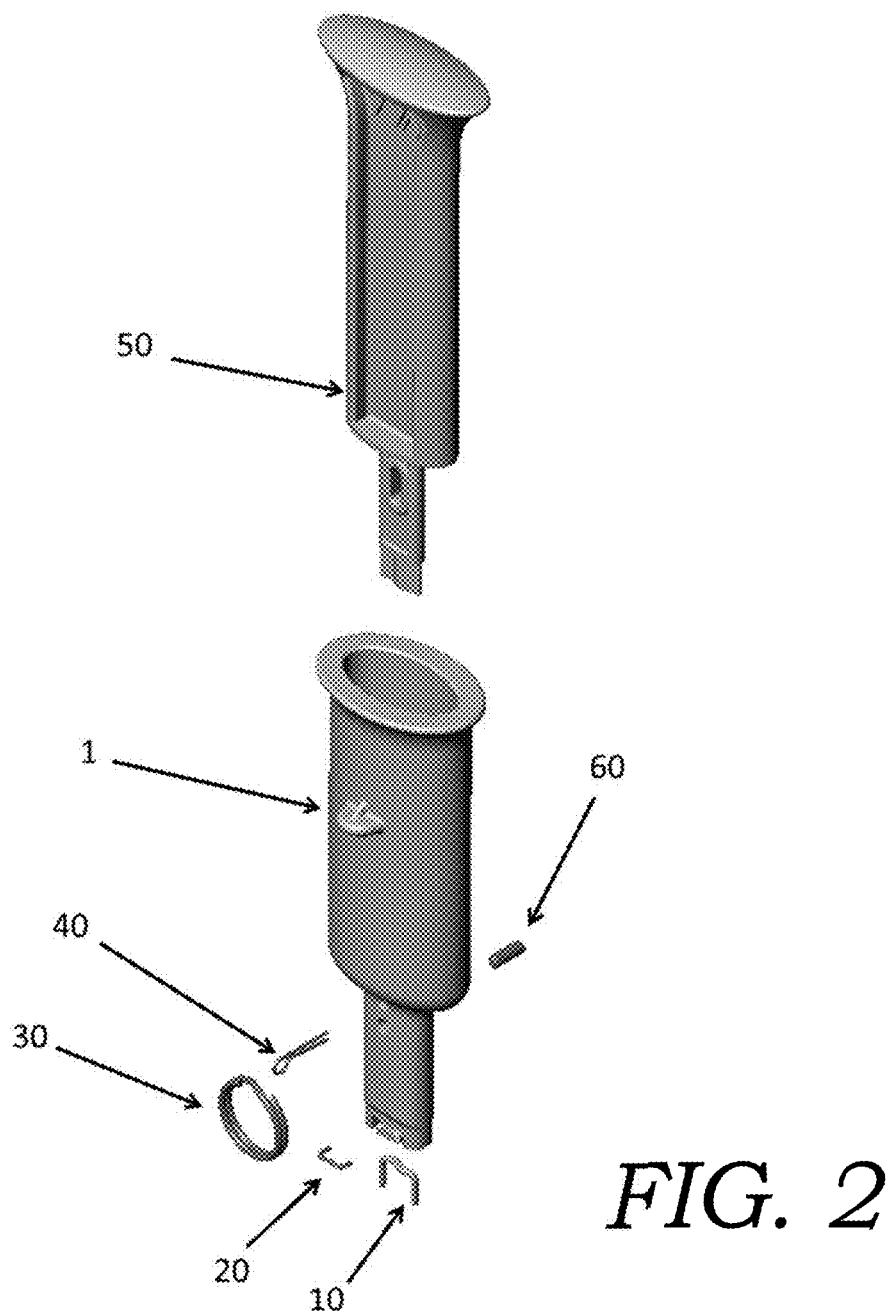
FIG. 2: An exploded view of the staple extrusion instrument illustrated in FIG. 1.

FIG. 2 is an illustration of an exploded view of the staple extrusion instrument illustrated in FIG. 1. FIG. 3A is an illustration of the staple extrusion instrument of FIG. 1 with the tip portion of the staple extrusion instrument circled. FIG. 3B is an illustration of a magnified view of the tip portion of the staple extrusion instrument circled in FIG. 3A. FIGS. 4A-4B are illustrations of different perspective views of the portion of the staple extrusion instrument of FIG. 1 focusing upon the portion holding staple 10. In each of FIGS. 1-2, 3A-3B, and 4A-4B, staple 10 is being held in the legs parallel shape with the bridge extended and, when released, will move to a non-parallel leg shape with the bridge contracted. For example, for a convergent staple 10, the legs will move to a convergent (closed) orientation when the staple is released from the cartridge.

FIG. 5 illustrates a perspective view of the portion of the staple extrusion instrument illustrated in FIG. 4B after staple 10 has been extruded.

In operation, the staple extrusion instrument of FIG. 1 can be utilized as follows. A drill guide (which has holes corresponding to the separation distance of the legs of the staple 10 being held in the staple extrusion instrument), is used to properly drills holes in bone in which the staple 10 is to be implanted. The staple extrusion instrument is used to line up the legs of staple 10 with the drilled holes. Before, during, or after this lining up process, the lock pin 40 (with the lock ring 30) is removed from the staple extrusion instrument. Extruder 50 is then advanced in cartridge 1. As shown in the orientation of FIG. 1 with the extruder 50 at the top of the cartridge 1, extruder 50 is moved in a downward direction relative to cartridge 1. By this motion, the extruder 50 contacts the bridge of staple 10 and further advancement of extruder 50 causes the bridge of staple 10 to push cartridge lever 20 causing it to swing down and out of the way while simultaneously pushing the staple 10 out of the cartridge 1 and into the bone. The disengagement of the staple 10 with the cartridge lever 20 transfers the staple force from the cartridge 1 to the bone (i.e., if the staple 10 were a convergent staple that was ejected into the air, rather than in bone, the staple would quickly move to a closed position).

It should be noted that for staple 10 that it may not be required (or necessary) to drill holes before implanting staple 10. Additionally, the extruder 50 can be durable such that it can be hammered upon to drive the staple 10 into bone.

Figure 6:
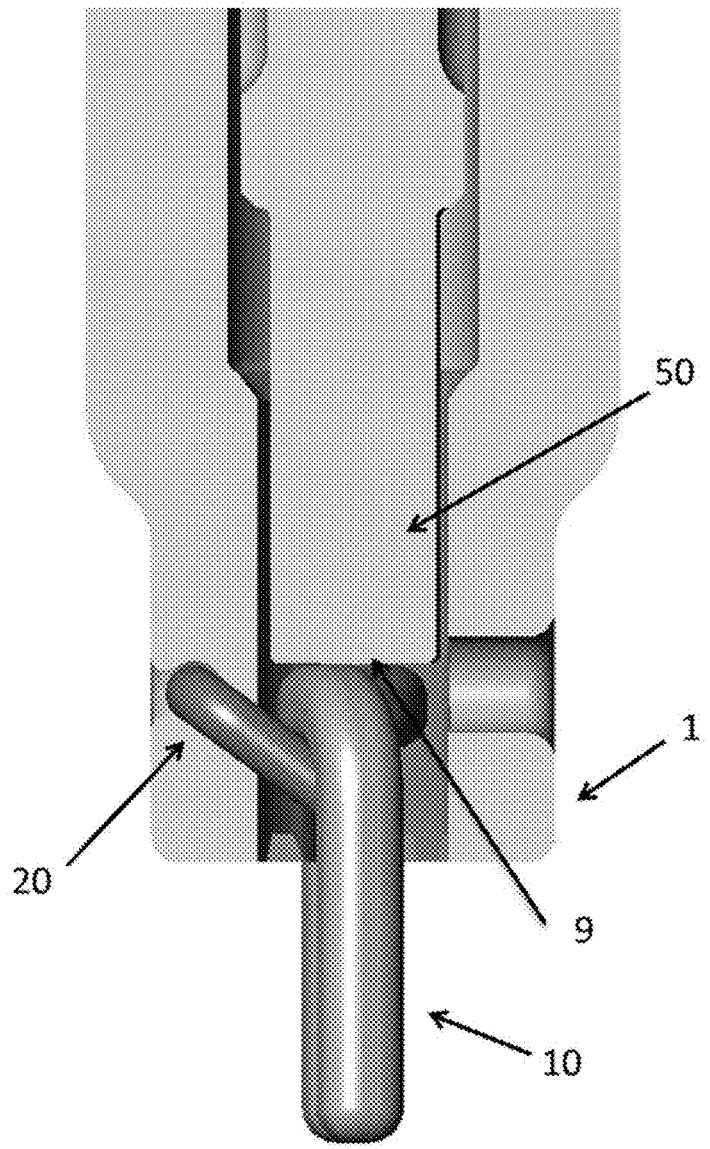
FIG. 6: A cross sectional side view of the portion of the staple extrusion instrument illustrated in FIG. 4B while the staple 10 is being extruded (an intermediate position).

FIG. 6 illustrates a cross sectional side view of the portion of the staple extrusion instrument illustrated in FIG. 4B while the staple 10 is being extruded (an intermediate position). This view shows the extruder face 9, which is the contact interface of extruder 50 to staple 10 that contacts and pushes staple 10 out with the advance of the extruder 50 in cartridge 1. As shown from the movement of cartridge lever 20, the lever must have an opening so that it can pivot down (in the orientation of the staple extrusion instrument) and away from the bridge of staple 10 such that the staple 10 can be disengaged from cartridge 1.

Wire Ring Cartridge

FIGS. 7A-7B and 8-10 are illustrations of an alternative embodiment of the present invention. In this embodiment, a release ring 70 is utilized in place of the cartridge levers 20 shown in FIG. 1.

Figure 7B:
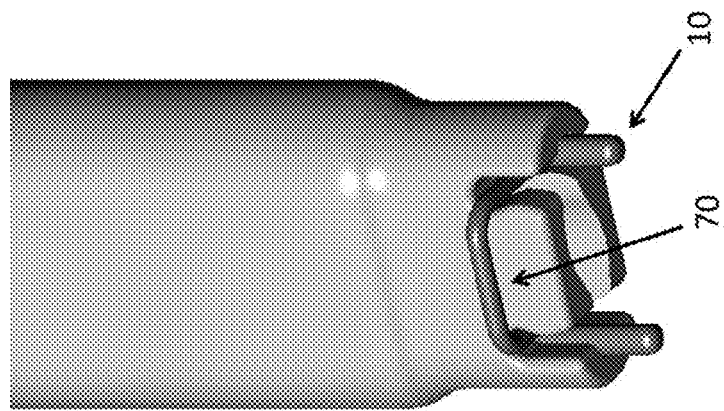
FIG. 7A-7B: Perspective views of an alternate staple extrusion instrument focusing upon the portion holding staple 10 of the staple extrusion instrument (similar to the portion shown in FIGS. 4A-4B). This embodiment of the staple extrusion instrument utilizes a release ring 70 that disengages the staple 10 from the cartridge 1 thereby transferring the staple force from the cartridge 1 to the structure into which the staple 10 is inserted.
Figure 7A:
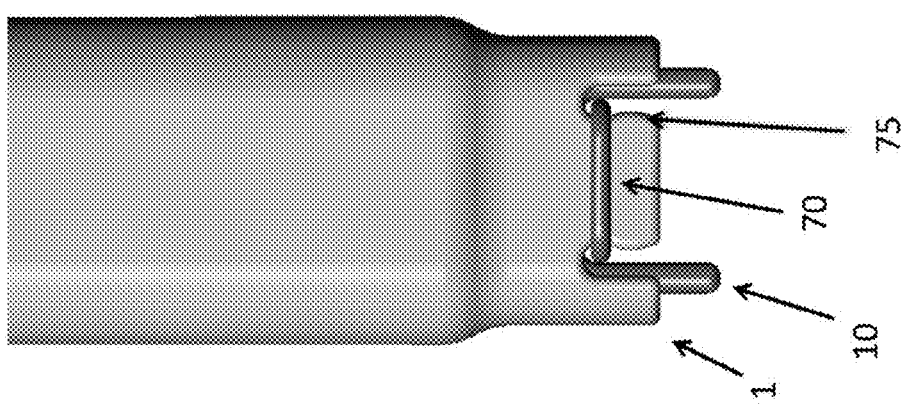

FIG. 7A-7B are illustrations of perspective views of this staple extrusion instrument, which focuses upon the portion holding staple 10 of the staple extrusion instrument (similar to the portion shown in FIGS. 4A-4B). This staple extrusion instrument utilizes a release ring 70 that disengages the staple 10 from the cartridge 1 thereby transferring the staple force from the cartridge 1 to the structure into which the staple 10 is inserted. In this embodiment, the extruder 50 can be a hand operated plunger that pushes staple 10 and release ring 70 to advance, release, and implant staple 10. Release ring 70 holds staple 10 open, and release ring 70 is pushed off by the staple 10 as the extruder 50 advances. Release ring 70 either drops separately during extrusion of staple 10 or may be under the bridge of staple 10 when released. In either case, the release ring 70 is recovered and can be discarded with the cartridge 1 after use.

Figure 8:
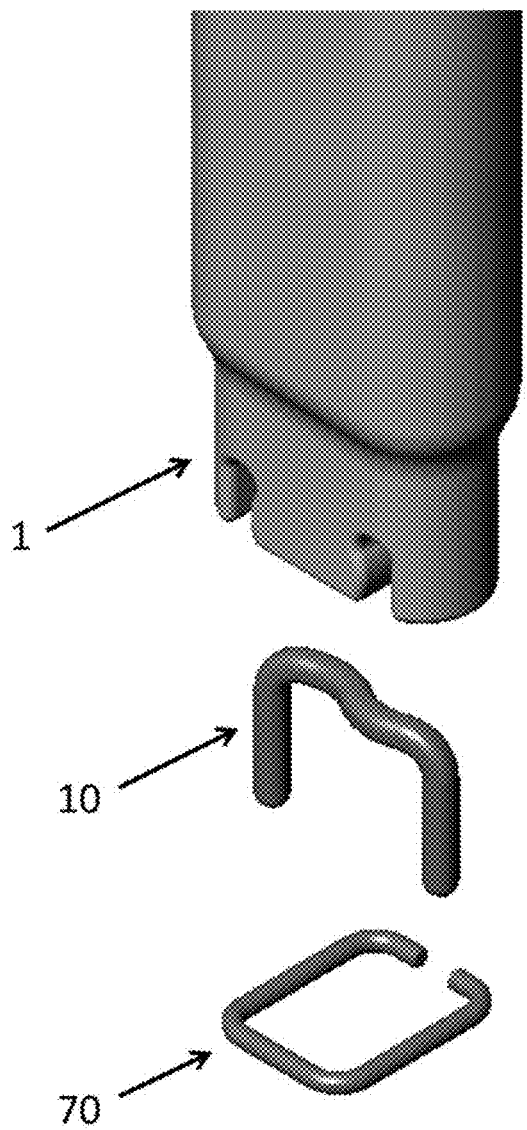
FIG. 8: An exploded view of the portion of the staple extrusion instrument illustrated in FIG. 7B.
Figure 9:
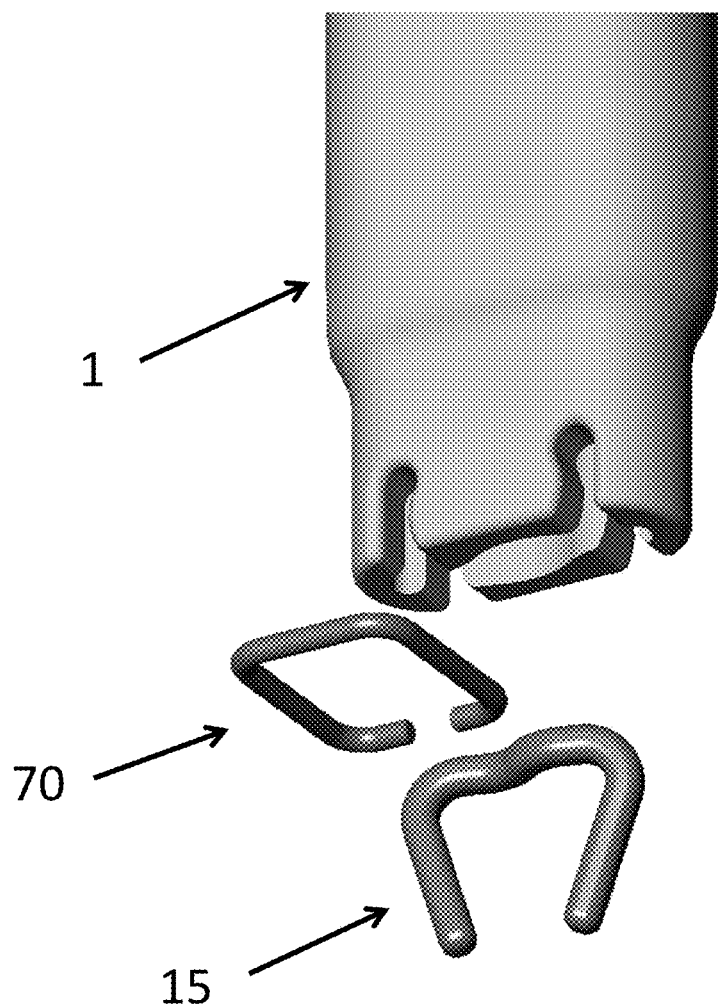
FIG. 9: A perspective view of the portion of the staple extrusion instrument illustrated in FIG. 7B after staple 10 has been extruded and changed shape to take the form of staple 15.

FIG. 8 is an illustration of an exploded view of the portion of the staple extrusion instrument illustrated in FIG. 7B. As shown in FIG. 8, the staple extrusion instrument has cartridge bumps 75 that are for retention of the release ring 70. FIG. 9 illustrates a perspective view of the portion of the staple extrusion instrument illustrated in FIG. 7B after staple 10 has been extruded. The shape and size of the bumps 75 can range from substantially no bump to visible bumps 75.

In operation, the staple extrusion instrument of FIG. 7A can be utilized similar to the staple extrusion instrument illustrated in FIG. 1. In this embodiment (of FIG. 7A), when extruder 50 is advanced in cartridge 1, the extruder 50 contacts the bridge of staple 10 and further advancement of extruder 50 causes the bridge of staple 10 to push on the release ring 70 causing release ring 70 to move so as to simultaneously push staple 10 out of the cartridge 1 and into the bone. Release ring 70 is retained by friction, grooves or bumps in the cartridge (such as cartridge bumps 75) and must strain (opening its cut section or straining due to the rings material properties) for the staple 10 to be released from cartridge 1. The disengagement of staple 1 with the release ring 70 transfers the staple force from the cartridge 1 to bone (i.e., if the staple 10 were a convergent staple that was ejected into the air, rather than in bone, the staple would quickly move to a closed position).

Figure 10:
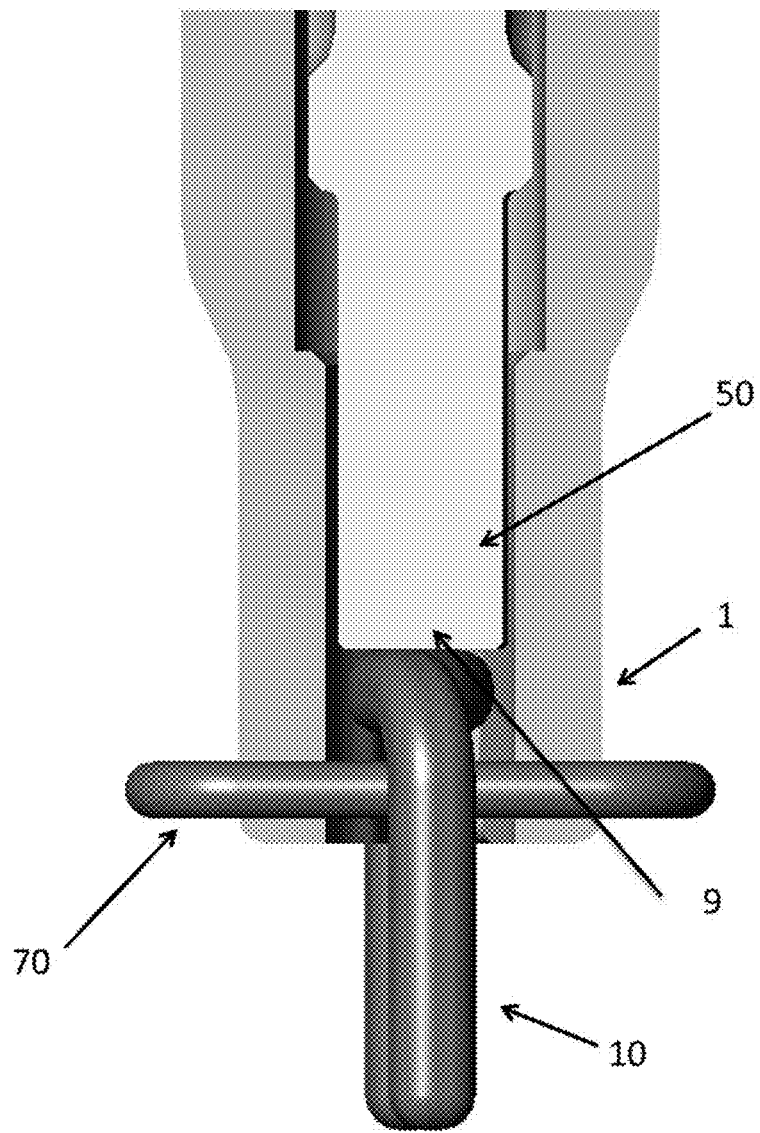
FIG. 10: A side view of the portion of the staple extrusion instrument illustrated in FIG. 7B while the staple 10 is prepared to be extruded (initial position).

FIG. 10 illustrates a side view of the portion of the staple extrusion instrument illustrated in FIG. 7B while the staple 10 is in position to be extruded (an initial position). This view shows the extruder face 9, which is the contact interface for extruder 50 to staple 10 that contacts and pushes the staple 10 out (with the release ring 70) with the advancement of the extruder 50 in cartridge 1.

With respect to the release ring 70, it can be made of metal. Alternatively or additionally, it can be made of other materials, such as plastic. Moreover, release ring 70 is illustrated as having an open section. This allows release ring 70 to expand over the bumps 75 while the staple 10 is being extruded. Alternatively release ring 70 having an open section, a second material (such as rubber or other stretchable material) can be used to close this open portion of release ring 70, where the second material will stretch during extrusion of the stable 10 to allow the release ring 70 expand to allow the staple to be extruded from the staple extrusion instrument.

Integral Cartridge Lever

FIGS. 11-12, 13A-13B, 14A-14B, and 15-16 are illustrations of another alternative embodiment of the present invention. In this embodiment, cartridge lever 3 is utilized in place of the cartridge lever 20 shown in FIG. 1 and the release ring 70 of FIG. 7A.

Figure 11:
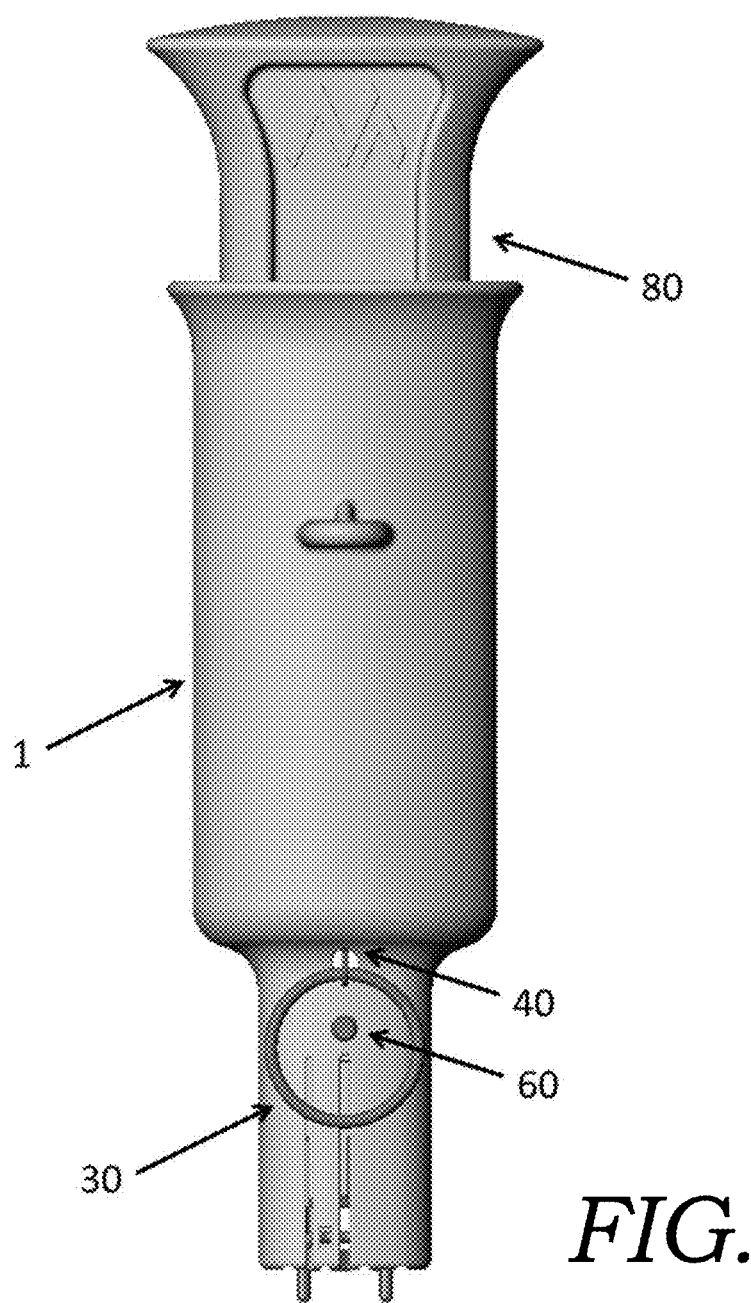
FIG. 11: Another alternate staple extrusion instrument in which the cartridge 1 holds the staple 10 in position until extruded from the cartridge 1. This embodiment of the staple extrusion instrument utilizes an integral cartridge lever 3 (shown in FIGS. 15 and 16) that disengages the staple 10 from the cartridge 1 thereby transferring the staple force from the cartridge 1 to the structure into which the staple 10 is inserted.

In the embodiment of FIG. 11, the staple extrusion instrument has a cartridge 1 that can be hand held and that holds the staple 10 in position until extruded from the cartridge 1. Cartridge 1 also holds the other elements of the staple extrusion instrument. This embodiment of the staple extrusion instrument utilizes a cartridge lever 3 (shown in FIGS. 15 and 16) that disengages the staple 10 from the cartridge 1 thereby transferring the staple force from the cartridge 1 to the structure into which the staple 10 is inserted. An extruder 80 fits within the cartridge 1 and can be moved relative to the cartridge 1. In the orientation of the FIG. 11 (with the extruder 80 at the top of the staple extrusion instrument), the extruder 80 can be moved downward. In this embodiment, extruder 80 is a hand operated plunger that pushes the mechanism (cartridge lever 3) and staple 10 to release and implant the staple 10. As with the other embodiments, this embodiment can include a lock pin ring 30, a lock pin 40, and a slide pin 60.

Figure 12:
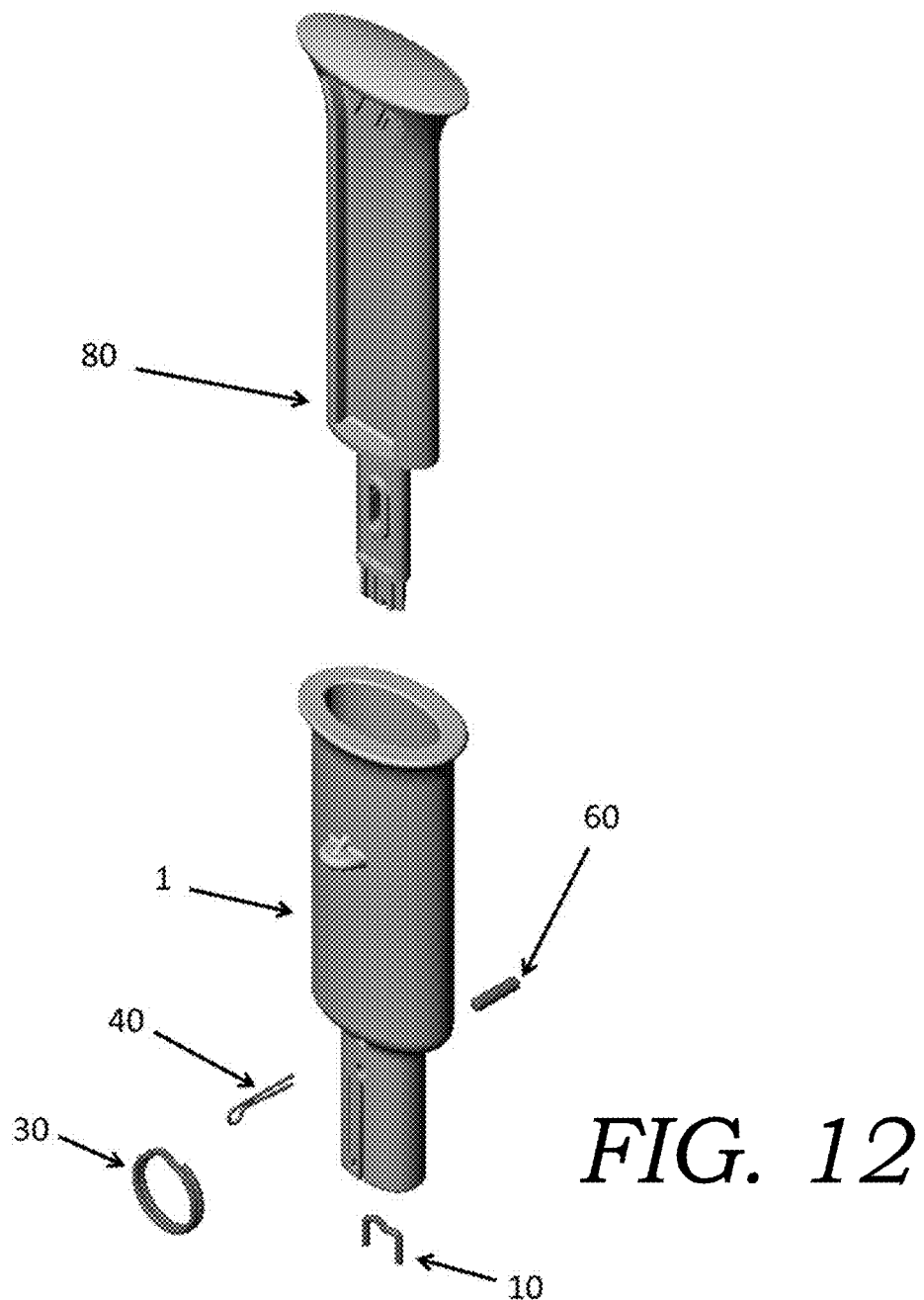
FIG. 12: An exploded view of the staple extrusion instrument illustrated in FIG. 11.
Figure 14A:
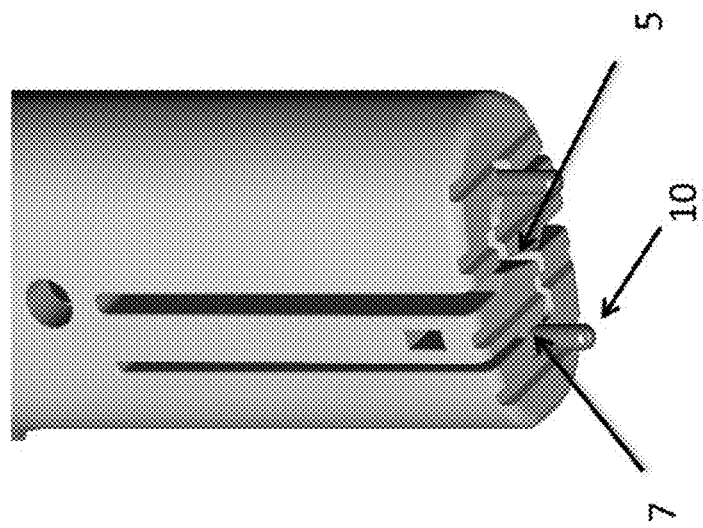
FIGS. 14A-14B: Perspective views of the portion of the staple extrusion instrument of FIG. 11 focusing upon the portion holding the staple 10.
Figure 14B:
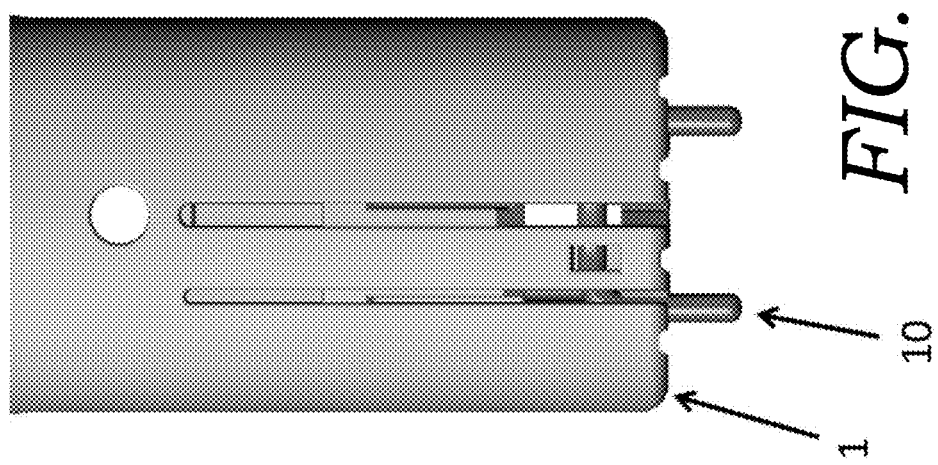

FIG. 12 is an illustration of an exploded view of the staple extrusion instrument illustrated in FIG. 11. FIG. 13A is an illustration of the staple extrusion instrument of FIG. 11 with the tip portion circled. FIG. 13B is an illustration of a magnified view of the tip portion of the staple extrusion instrument circled in FIG. 13A. FIGS. 14A-14B are illustrations of different perspective views of the portion of the staple extrusion instrument of FIG. 11 focusing upon the portion holding staple 10. As shown in FIG. 14B, the staple extrusion instrument has a lever face angle 5 and lever bumps 7.

Lever face angles 5 are designed to move along the path of staple 10 as it is moving from a parallel shape to a non-parallel shape (i.e., when staple 10 is a convergent stable, lever face angles 5 are designed to move allow the path of transition of staple 10 as it is moving from an open shape to a closed shape). Lever face angles 5 can be selected from a range of angles to allow the staple extrusion instrument and its cartridge lever 3 to control the extrusion force and the bone force as the staple 10 is being implanted.

Lever bumps 7 are generally located at the junction of each of the legs of the staple 10 and the bridge of the staple 10. Lever bumps 7 control the extrusion breakout release force (i.e., the force that needs to be applied before the staple 10 is released and the legs of the staple 10 begin to move).

Figure 15:
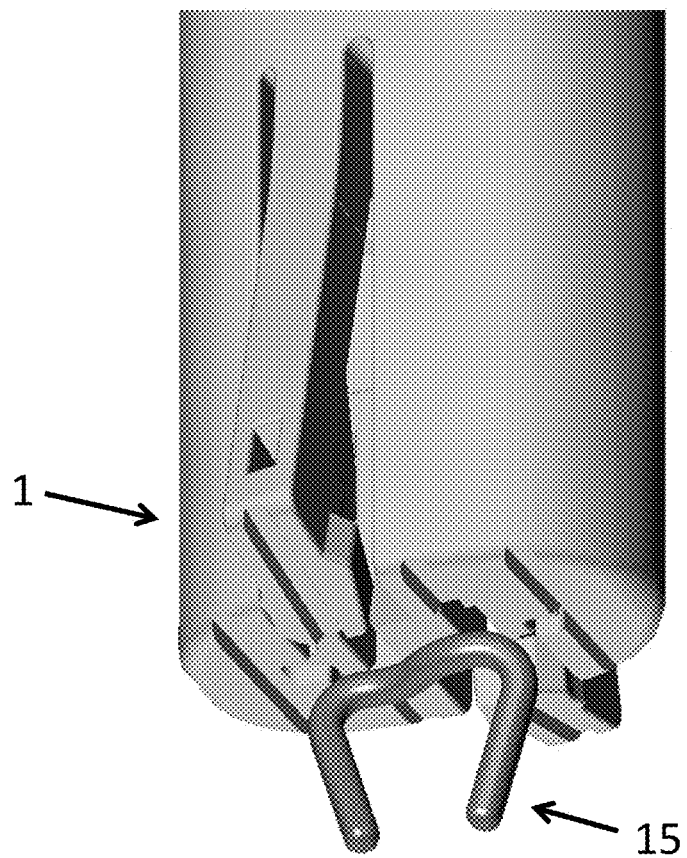
FIG. 15: A perspective view of the portion of the staple extrusion instrument illustrated in FIG. 14B after the lever 3 has deflected outward and the staple 10 has been extruded to change to its closed staple 15 shape.

FIG. 15 illustrates a perspective view of the portion of the staple extrusion instrument illustrated in FIG. 14B after staple 10 has been extruded. Cartridge lever 3 is shown as a one or more levers holding the staple 10 until cartridge lever 3 is swung out and into release position through the sliding contact of the advancing extruder 80.

In operation, the staple extrusion instrument of FIG. 11 can be utilized similar to the staple extrusion instruments illustrated in FIGS. 1 and 7A. In this embodiment (of FIG. 11), when extruder 80 is advanced in cartridge 1, the extruder 80 contacts the ramp of the cartridge lever 3 and further advancement of extruder 80 causes the cartridge levers 3 to swing outward while simultaneously pushing staple 10 out of the cartridge 1 and into the bone. The disengagement of staple 10 with the cartridge lever 3 transfers the staple force from the cartridge 1 to bone (i.e., if the staple 10 were a convergent staple that was ejected into the air, rather than in bone, the staple would quickly move to a closed position). Cartridge lever face angle 5 controls the transfer of staple force to bone during extrusion of staple 10 from cartridge 1.

Figure 16:
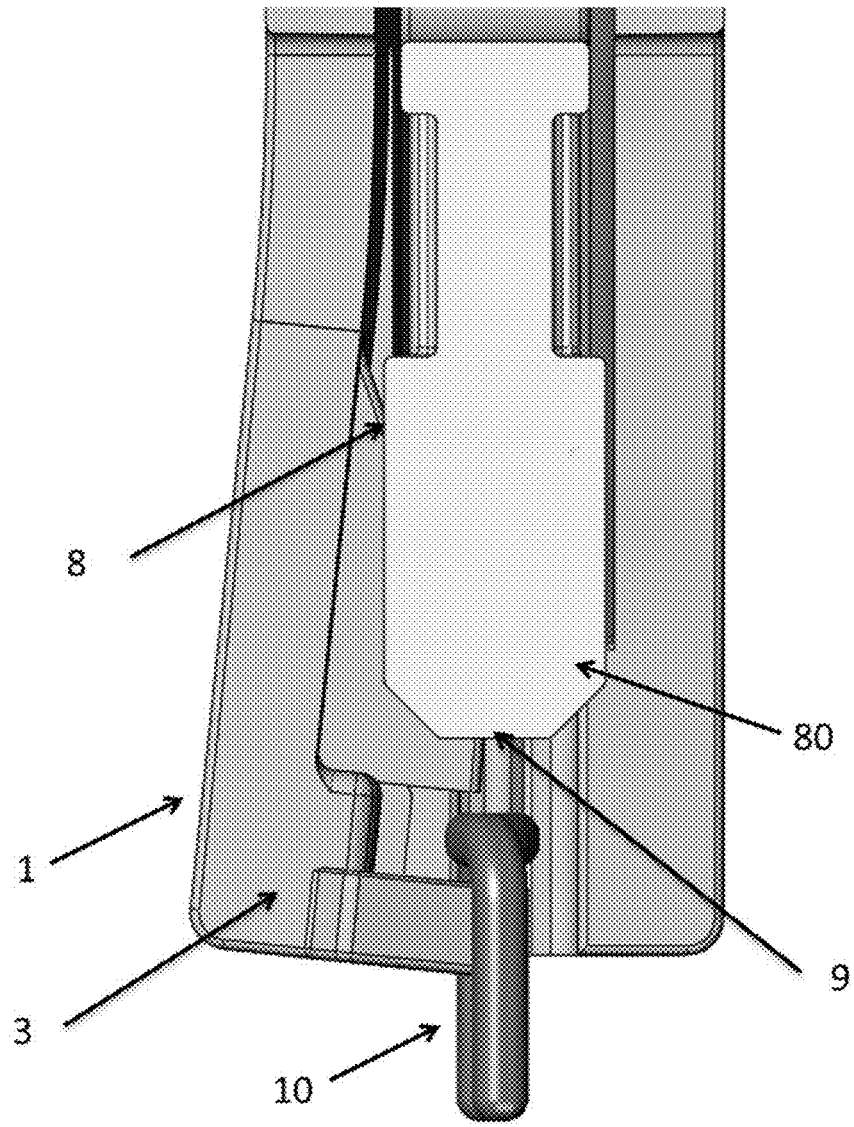
FIG. 16: A cross sectional side view of the portion of the staple extrusion instrument illustrated in FIG. 14B while the staple 10 is being extruded (an intermediate position).

FIG. 16 illustrates a cross sectional side view of the portion of the staple extrusion instrument illustrated in FIG. 14B while the staple 10 is being extruded (an intermediate position). This view shows extruder face 9, which is the contact interface of extruder 80 to staple 10 that contacts and pushes staple 10 out with the advance of the extruder 80 in cartridge 1. Lever ramp 8 is also shown, which is the contact interface of the extruder 80 so as to swing the cartridge lever 3 outward as the extruder 80 is advanced.

Manufacture of Staple Extrusion Instrument

For embodiments of the present invention, the various components of the staple extrusion instrument (cartridge, cartridge levers, extruder, lock pin assembly, level face angle, etc.) can be designed and manufactured by one of ordinary skill in the art. The materials from which these are made include plastics (such as thermoplastic polymers), metals, and other like materials.

As for the staples, these staples can be made of various configurations depending upon the bone in which they are to be implanted. The staples are formed such that when held in a parallel shape, the staple has stored energy at room temperature such that, when released, the staple will move to a non-parallel shape (either convergent or divergent). Examples of such staple shapes are described in the PCT '539 patent Application.

For instance, staple 10 can have a bridge such that, at room temperature, there is a strain in the bridge and corners that stores energy by (1) stretching molecular bonds within their recoverable elastic range; (2) creating recoverable stress induced martensite in its structure if fabricated from a shape memory metal, such as nitinol; and/or (3) creating recovered temperature induced forces, again, if the structure is fabricated from a shape memory metal, such as nitinol.

With respect to the first of these types of staples, this linear elastic behavior (caused by the stretching of molecular bonds) is common to spring tempered metals, including, but not limited to, stainless steel, titanium, nickel-chromium alloys (such as Inconel alloys), memory shaped materials (such as nitinol), and other alloys. This is behavior is referred to as "elastic deformation" in that once the strain is removed, the molecules will no longer remained stretched and substantially return to their original position (thus releasing the stored energy).

With respect to the second of these types, this change of structure occurs in certain materials, such as shape memory metals (like nitinol) that can transform from one structure form to another structure form. Shape memory materials, like nitinol, have an austenite phase (cubic B2 structure) and a martensite phase (monoclinic B19' structure). Strain in the bridge and corners of the staple can cause stress induced transformation of the shape memory metal such that a portion of the shape metal material (such as in the bridge and the corners) will transform from austenite to martensite. This behavior is referred to as "pseudo elastic deformation" in that once the strain is removed, the shape memory material will return to austenite, and the material will substantially return to its original position (thus releasing the stored energy). When pseudo elastic deformation (and elastic deformation) occurs before any substantial conventional plasticity, the shape memory material is referred to as exhibiting "super elasticity."

Over-stretching either of these two types of staples can lead to formation of permanent deformation that renders the material incapable of returning completely to its original shape (or for reverting to austenite). This behavior is referred to as "plastic deformation" and also "permanent deformation" in that when the strain is removed the material that is permanently deformed will not substantially return to its original shape. The combined behavior of elastic deformation and pseudo elastic deformation are sometimes referred to collectively as "non-plastic deformation" and "non-permanent deformation."

It should be noted that a material can be plastically deformed in some portions and non-plastically deformed in other portions. Indeed, the non-plastic deformations may itself be a combination of elastic deformations and pseudo-elastic deformations. Thus, a material under strain could deform having a plastic deformation component, a non-plastic deformation component, and a pseudo elastic deformation component. For materials that do not change phase under stress, the pseudo elastic deformation component would basically be zero.

As the amount of non-plastic deformation component increases versus the amount of plastic deformation component, the more the material will tend to move toward its original shape (i.e., return toward its original shape) when the strain is removed.

For instance, when the plastic deformation component is insubstantial (i.e., the material will substantially return to its original shape when the strain is removed), the deformation components are substantially all non-plastic deformation components. In the present application, there is "no substantial plastic deformation" when the material is substantially able to return to its original configuration after the stain is removed (i.e., the plastic deformation component is basically insubstantial when compared to the non-plastic deformation component). In certain of the staples that can be used in embodiments of the present invention, the strain in the bridge and corners stores energy with no substantial deformation of the staple (including no substantial deformation of the bridge and corners).

Alternatively, for instance, the deformation may include both a substantial plastic deformation component and a substantial non-plastic deformation component. A material could be plastically deformed to a degree that it cannot return to its original shape once the strain is removed; but, the material could still tend to move back toward (but not completely) to its original shape when the strain is removed. Strain in the bridge and corners could store energy due to non-plastic deformation (substantial elastic and/or pseudo elastic deformation) can occur even when there is substantial plastic deformation of the staple. Thus, in some of the staples used with embodiments of the present invention, the strain in the bridge and corners stores energy even when there is substantial deformation of the staple (including substantial deformation of the bridge and/or corners). Generally, such materials are not shaped memory metals, but usually other materials that exhibit substantial elastic deformation components even when deformed in conjunction with plastic deformation of the material.

With respect to the staples of types (1) (stretching molecular bonds within their recoverable elastic range) and (2) (creating recoverable stress induced martensite in its structure), the staple can be moved mechanically from the non-parallel position to the parallel position (such as by pliers) and then loaded onto the cartridge. In such case, the staple is being restrained by the cartridge with forces that will be transferred to from the cartridge to the bone when the staple is released. Such forces are "stress induced" in that the stress has been mechanically formed by mechanically moving the staple before insertion in the staple extrusion instrument.

As to the staples of type (3) (creating recovered temperature induced forces), this is also a staple made from a memory shape metal, such as nitinol. This staple can be manufactured so that it is in one shape at a cold temperature that is well below room temperature (such as below 0° C.) (martensite phase) and that will move to a different shape at room temperature (austenite phase). For example, such a staple could be a convergent staple made of nitinol that is in an open condition (martensite phase) below room temperature and that will want to move to a closed position (austenite phase) at some higher temperature that is at or, more optimally, at or below room temperature.

Using a staple of type (3), it is typically placed into the staple extrusion instrument while still at a low enough temperature that it remains in the open position. By doing so, the staple can be readily loaded into the staple extrusion instrument with little difficulty as the staple is then fixed in the open shape (and thus there is need to use pliers or other mechanical forces to hold open the staple). Once the staple is restrained within the cartridge of the staple extrusion instrument, the staple is allowed to rise in temperature above the martensite to austenite phase transition. Generally, this is done by allowing the staple to warm due to room conditions.

Once the temperature rises above this transition temperature, the staple will want to undergo a phase transition (from martensite to austenite) and move to its non-parallel (closed) position. However, since the cartridge is restraining the staple and keeping the staple in its parallel (open) position, the staple will now have "stressed restrained" forces due to this change in temperature. The staple will remain in such an open position until extruded from the cartridge, at which time the restraints of the cartridge will be released, allowing the staple to move toward its closed position.

Staple Extrusion Instrument Kit

Figure 17:
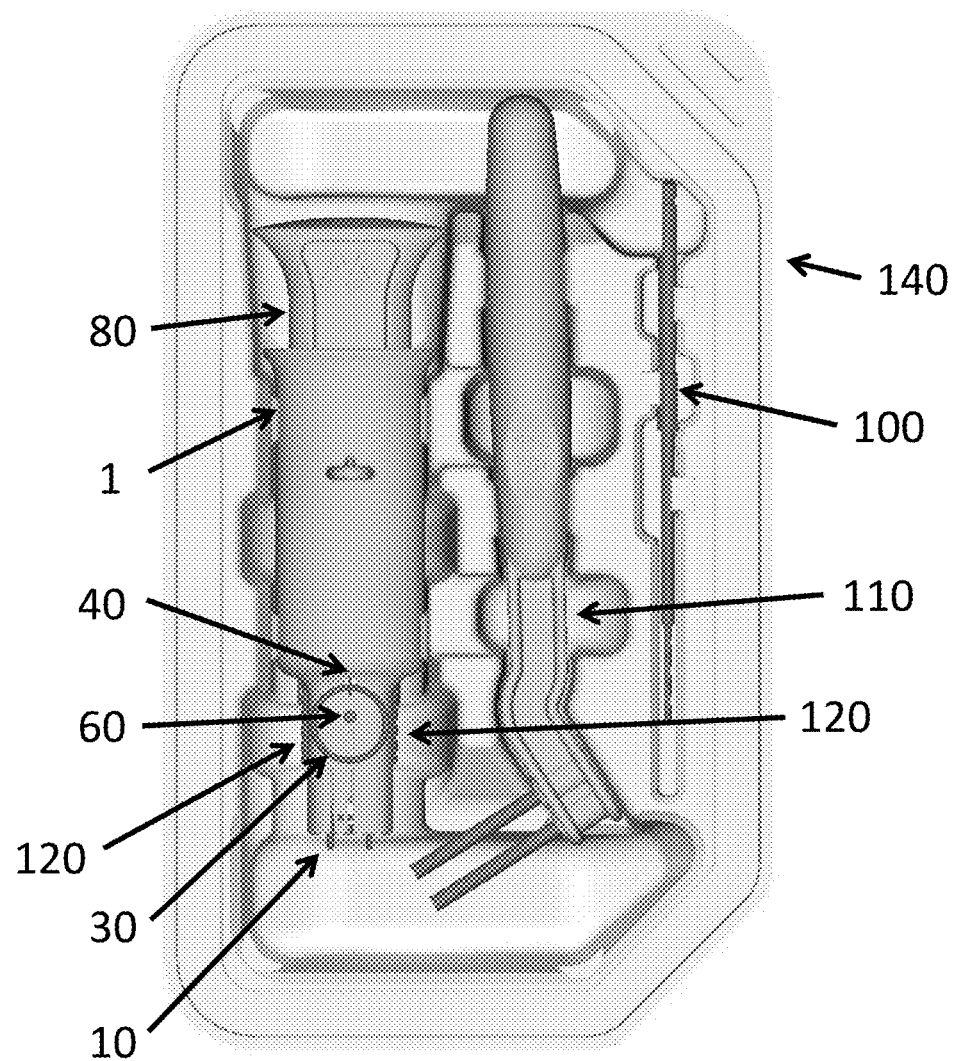
FIG. 17: A package for sterilization, storage, delivery of the staple and instruments and use in the operative field.
Figure 18:
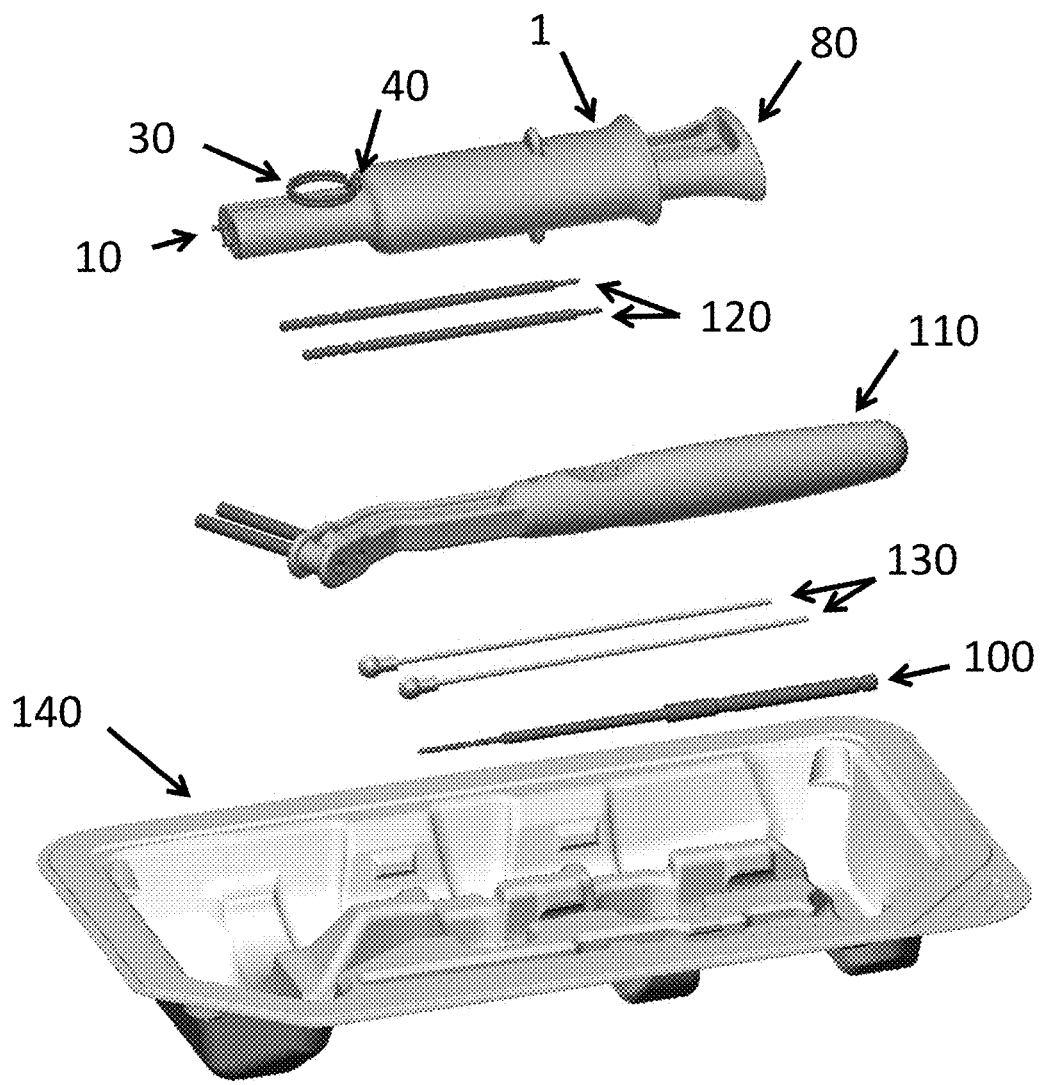
FIG. 18: An exploded view of the package of FIG. 17.

To reduce hospital handling cost and minimize the incidence of hospital related infections embodiments of the subject invention can be provided in a kit that includes a staple extrusion instrument in which the cartridge 1 holds the staple 10 in position. While the kit can only include the staple extrusion instrument, the kit may also include one or more of a drill bit 100, a drill guide 110, drill hole locating pins 120, and bone fixation wires 140, such as shown in FIG. 17 (and the exploded view of the kit shown in FIG. 18). This kit can be delivered to the hospital in a quality controlled sterile package 140, maintains the staple, the staple extrusion instrument, and other instruments for use in the operative field.

Although the description above contains many specificities, these should not be construed as limiting the scope of the embodiments but as merely providing illustrations of some of the presently preferred embodiments. Thus the scope of the embodiment should be determined by the appended claims and their legal equivalents, rather than by the examples given.

The disclosures of all patents, patent applications, and publications cited herein are hereby incorporated herein by reference in their entirety, to the extent that they provide exemplary, procedural, or other details supplementary to those set forth herein.

What is claimed is:

1. A bone staple extrusion instrument comprising:
   (a) a bone staple;
   (b) a cartridge that restrains the bone staple such that the bone staple is maintained in a first position, wherein
      (i) the bone staple is operable for spontaneously moving to a second position when released from the cartridge,
      (ii) the bone staple is operable for moving from the first position to the second position,
      (iii) the bone staple comprises a bridge and legs,
      (iv) the bone staple is in the first position when the legs of the bone staple are substantially parallel,
      (v) the bone staple is in the second position when the legs of the bone staple are substantially non-parallel, and
      (vi) the cartridge comprises a movable actuator that holds the bone staple in the cartridge restrained in the first position, wherein the movable actuator comprises a component selected from the group consisting of
         (A) a lever movably integrated into the cartridge,
         (B) a wire lever, and
         (C) a wire ring that can be separated from the other portions of the cartridge; and
   (c) an extruder operatively connected to the cartridge, wherein the extruder is operable for moving relative to the cartridge to cause extrusion from the cartridge of the bone staple being restrained by the cartridge.

2. The bone staple extrusion instrument of claim 1, wherein the movable actuator comprises the lever movably integrated into the cartridge.

3. The bone staple extrusion instrument of claim 1, wherein the movable actuator comprises the wire lever.

4. The bone staple extrusion instrument of claim 1, wherein the movable actuator comprises the wire ring that can be separated from the other portions of the cartridge.

5. The bone staple extrusion instrument of claim 1, wherein the extruder is operable for moving the movable actuator causing the bone staple to be extruded from the cartridge.

6. The bone staple extrusion instrument of claim 5, wherein the extruder is operable for directly contacting the movable actuator.

7. The bone staple extrusion instrument of claim 5, wherein
   (a) the extruder is operable for directly contacting the bone staple, and
   (b) the bone staple is operable for directly contacting the movable actuator.

8. The bone staple extrusion instrument of claim 1, wherein the bone staple comprises memory shape metal.

9. The bone staple extrusion instrument of claim 8, wherein the bone staple comprises stress induced memory shape metal in a martensite phase.

10. The bone staple extrusion instrument of claim 8, wherein
    (a) the bone staple has stress induced forces that are being restrained by the cartridge; and
    (b) the stress induced forces are operable for spontaneously moving the bone staple from the first position to the second position when released from the cartridge.

11. The bone staple extrusion instrument of claim 8, wherein the bone staple comprises stress restrained memory shape metal in a martensite phase.

12. The bone staple extrusion instrument of claim 8, wherein
    (a) the bone staple has temperature induced forces that are being restrained by the cartridge; and
    (b) the temperature induced forces are operable for spontaneously moving the bone staple from the first position to the second position when released from the cartridge.

13. The bone staple extrusion instrument of claim 1, wherein
    (a) the bone staple has stress induced forces that are being restrained by the cartridge; and
    (b) the stress induced forces are operable for spontaneously moving the bone staple from the first position to the second position when released from the cartridge.

14. The bone staple extrusion instrument of claim 1, wherein the cartridge further comprises a lock pin assembly operatively connected to the movable actuator to prevent the extrusion of the bone staple from the cartridge until removed.

15. The bone staple extrusion instrument of claim 1, wherein the bone staple is operable for moving from the first position to the second position without substantial plastic deformation of the bone staple.

16. The bone staple extrusion instrument of claim 1, wherein the bone staple extrusion instrument comprises only one bone staple.

17. The bone staple extrusion instrument of claim 1, wherein the extruder is a hand operated plunger.

18. A bone staple extrusion instrument comprising:
    (a) a bone staple;
    (b) a cartridge that restrains the bone staple such that the bone staple is maintained in a first position, wherein
       (i) the bone staple is operable for spontaneously moving to a second position when released from the cartridge,
       (ii) the bone staple is operable for moving from the first position to the second position,
       (iii) the bone staple comprises a bridge and legs,
       (iv) the bone staple is in the first position when the legs of the bone staple are substantially parallel,
       (v) the bone staple is in the second position when the legs of the bone staple are substantially non-parallel, (vi) the cartridge comprises a movable actuator that holds the bone staple in the cartridge restrained in the first position,
(vii) the cartridge comprises a lock pin assembly operatively connected to the movable actuator to prevent the extrusion of the bone staple from the cartridge until removed,
(viii) the lock pin assembly comprises a lock pin and a lock ring, and
(c) an extruder operatively connected to the cartridge, wherein the extruder is operable for moving relative to the cartridge to cause extrusion from the cartridge of the bone staple being restrained by the cartridge.

19. A bone staple extrusion instrument comprising:
(a) a bone staple;
(b) a cartridge that restrains the bone staple such that the bone staple is maintained in a first position, wherein
(i) the bone staple is operable for spontaneously moving to a second position when released from the cartridge,
(ii) the bone staple is operable for moving from the first position to the second position,
(iii) the bone staple comprises a bridge and legs;
(iv) the bone staple is in the first position when the legs of the bone staple are substantially parallel,
(v) the bone staple is in the second position when the legs of the bone staple are substantially non-parallel, and
(vi) the cartridge comprises a lever movably integrated into the cartridge and that holds the bone staple in the cartridge restrained in the first position; and
(c) an extruder operatively connected to the cartridge, wherein
(i) the extruder is operable for moving the lever to release the lever from holding the bone staple in the cartridge, and
(ii) the extruder is operable for moving relative to the cartridge to cause extrusion from the cartridge of the bone staple being restrained by the cartridge.

20. The bone staple extrusion instrument of claim 19, wherein the bone staple comprises stress induced memory shape metal in a martensite phase.

21. The bone staple extrusion instrument of claim 19, wherein the bone staple comprises stress restrained memory shape metal in a martensite phase.

22. The bone staple extrusion instrument of claim 19, wherein the cartridge further comprises a lock pin assembly operatively connected to the movable actuator to prevent the lever from moving to release the bone staple from the cartridge.

23. The bone staple extrusion instrument of claim 19, wherein the bone staple extrusion instrument comprises only one bone staple.

24. The bone staple extrusion instrument of claim 19, wherein the extruder is a hand operated plunger.

* * * * *